United States Patent
Ingimundarson et al.

(10) Patent No.: US 9,572,705 B2
(45) Date of Patent: Feb. 21, 2017

(54) SPINAL ORTHOSIS

(71) Applicant: OSSUR HF, Reykjavik (IS)

(72) Inventors: Arni Thor Ingimundarson, Gardabaer (IS); Nina Bakken, Oslo (NO); Bjorn Omarsson, Reykjavik (IS); Harry Duane Romo, Aliso Viejo, CA (US); Jeff Nemeth, Chandler, AZ (US)

(73) Assignee: OSSUR HF, Reykjavik (IS)

( * ) Notice: Subject to any disclaimer, the term of this patent is extended or adjusted under 35 U.S.C. 154(b) by 578 days.

(21) Appl. No.: 14/030,323

(22) Filed: Sep. 18, 2013

(65) Prior Publication Data

US 2014/0018715 A1 Jan. 16, 2014

Related U.S. Application Data

(63) Continuation-in-part of application No. 13/739,508, filed on Jan. 11, 2013, now Pat. No. 9,370,440.

(60) Provisional application No. 61/711,435, filed on Oct. 9, 2012, provisional application No. 61/650,684, filed on May 23, 2012, provisional application No. 61/586,167, filed on Jan. 13, 2012.

(51) Int. Cl.
*A61F 5/02* (2006.01)

(52) U.S. Cl.
CPC ............... *A61F 5/026* (2013.01); *A61F 5/028* (2013.01)

(58) Field of Classification Search
CPC .... A61F 5/055; A61F 5/05816; A61F 5/3707; A61F 5/012; A61F 5/05891; A61F 5/024; A61F 5/026; A61F 5/028; A61F 5/03; A61F 13/14

See application file for complete search history.

(56) References Cited

U.S. PATENT DOCUMENTS

| | | | |
|---|---|---|---|
| 7,916 A | 1/1851 | Knapp |
| 61,487 A | 1/1867 | Vollschwitz |
| 181,948 A | 9/1876 | Kleinschuster |
| 232,420 A | 9/1880 | Smith |
| 321,145 A | 6/1885 | Spencer |
| 321,146 A | 6/1885 | Spencer |
| 328,638 A | 10/1885 | Battershall |
| 368,699 A | 8/1887 | Zervas |
| 386,642 A | 7/1888 | Mann |
| 507,172 A | 10/1893 | Shelden |

(Continued)

FOREIGN PATENT DOCUMENTS

| AU | 2010271020 A1 | 2/2012 |
| AU | 2010271020 A2 | 2/2012 |

(Continued)

OTHER PUBLICATIONS

Silosheath Brochure, Soft Socket Gel Liner, 4 pages, 1994.

(Continued)

*Primary Examiner* — Ophelia A Hawthorne
(74) *Attorney, Agent, or Firm* — Workman Nydegger

(57) ABSTRACT

A spinal orthosis has an elongate and substantially rigid spinal frame having upper, middle and lower portions, and a lumbar assembly connected to the lower portion of the spinal frame. A strap assembly secures to an upper portion of the spinal frame and is adjustably secured to the lumbar assembly. An elastic strap has a first end secured to the spinal frame and a second end adjustably securing to the lumbar assembly.

19 Claims, 15 Drawing Sheets

(56) References Cited

U.S. PATENT DOCUMENTS

| | | |
|---|---|---|
| 571,749 A | 11/1896 | Colton |
| 596,849 A | 1/1898 | Combier |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 746,563 A | 12/1903 | McMahon |
| 772,926 A | 10/1904 | Colton |
| 787,894 A | 4/1905 | Colton |
| 888,490 A | 5/1908 | Haas |
| 894,066 A | 7/1908 | Scapra |
| 980,457 A | 1/1911 | Toles |
| 1,124,596 A | 1/1915 | Dalpe |
| 1,316,915 A | 9/1919 | Meyer et al. |
| 1,393,188 A | 10/1921 | Whiteman |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,755,641 A | 4/1930 | Foulke |
| 1,948,785 A | 2/1934 | Dondelinger |
| 1,981,157 A | 11/1934 | Walter |
| 2,036,484 A | 4/1936 | Le May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease, Jr. |
| 2,543,370 A | 2/1951 | Kludt et al. |
| 2,554,337 A | 5/1951 | Lampert |
| 2,630,801 A | 3/1953 | Mest et al. |
| 2,808,050 A | 7/1954 | Ward |
| 2,696,011 A | 12/1954 | Galdik |
| 2,749,550 A | 6/1956 | Pease |
| 2,793,368 A | 5/1957 | Nouel |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Davidson et al. |
| 3,096,760 A | 7/1963 | Nelkin |
| 3,128,514 A | 4/1964 | Parker et al. |
| 3,274,996 A | 9/1966 | Jewett |
| 3,282,264 A | 11/1966 | Connelly |
| 3,351,053 A | 11/1967 | Stuttle |
| 3,371,351 A | 3/1968 | Allain |
| 3,434,469 A | 3/1969 | Swift |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A | 5/1971 | Schultz |
| 3,600,717 A | 8/1971 | McKeehan |
| 3,601,819 A | 8/1971 | Herrmann |
| 3,762,421 A | 10/1973 | Sax, Sr. |
| 3,771,513 A | 11/1973 | Velazquez |
| 3,793,749 A | 2/1974 | Gertsch et al. |
| 3,808,644 A | 5/1974 | Schoch |
| 3,812,850 A | 5/1974 | Reiman |
| 3,816,211 A | 6/1974 | Haigh |
| 3,834,048 A | 9/1974 | Maurer |
| 3,889,664 A | 6/1975 | Heuser et al. |
| 3,902,503 A | 9/1975 | Gaylord, Jr. |
| 3,920,008 A | 11/1975 | Lehman |
| 3,926,182 A | 12/1975 | Stabholz |
| 3,927,665 A | 12/1975 | Wax |
| 3,945,376 A | 3/1976 | Kuehnegger |
| 4,042,433 A | 8/1977 | Hardy et al. |
| 4,055,168 A | 10/1977 | Miller et al. |
| 4,071,387 A | 1/1978 | Schlaepfer |
| 4,099,524 A | 7/1978 | Cueman et al. |
| 4,114,788 A | 9/1978 | Zufich |
| 4,173,973 A | 11/1979 | Hendricks |
| 4,175,553 A | 11/1979 | Rosenberg |
| 4,230,101 A | 10/1980 | Gold |
| 4,261,081 A | 4/1981 | Lott |
| 4,285,336 A | 8/1981 | Oebser et al. |
| 4,383,523 A | 5/1983 | Schurman |
| 4,392,489 A | 7/1983 | Wagner, Sr. |
| 4,433,456 A | 2/1984 | Baggio |
| RE31,564 E | 4/1984 | Hendricks |
| 4,475,543 A | 10/1984 | Brooks et al. |
| 4,494,536 A | 1/1985 | Latenser |
| 4,502,471 A | 3/1985 | Owens |
| 4,508,110 A | 4/1985 | Modglin |
| 4,555,830 A | 12/1985 | Petrini et al. |
| 4,559,933 A | 12/1985 | Batard et al. |
| 4,569,336 A | 2/1986 | Wheeler |
| 4,574,500 A | 3/1986 | Aldinio et al. |
| 4,574,789 A | 3/1986 | Forster |
| 4,574,790 A | 3/1986 | Wellershaus |
| 4,608,971 A | 9/1986 | Borschneck |
| 4,616,524 A | 10/1986 | Bidoia |
| 4,619,657 A | 10/1986 | Keates et al. |
| 4,628,913 A | 12/1986 | Lerman |
| 4,631,839 A | 12/1986 | Bonetti et al. |
| 4,631,840 A | 12/1986 | Gamm |
| 4,635,626 A | 1/1987 | Lerman |
| 4,640,269 A | 2/1987 | Goins |
| 4,648,390 A | 3/1987 | Friddle |
| 4,649,574 A | 3/1987 | Michels |
| 4,654,985 A | 4/1987 | Chalmers |
| 4,658,807 A | 4/1987 | Swain |
| 4,660,302 A | 4/1987 | Arieh et al. |
| 4,677,699 A | 7/1987 | Barabe |
| 4,677,969 A | 7/1987 | Calabrese |
| 4,680,878 A | 7/1987 | Pozzobon et al. |
| 4,691,696 A | 9/1987 | Farfan de los Godos |
| 4,696,291 A | 9/1987 | Tyo |
| 4,697,592 A | 10/1987 | Maddux et al. |
| 4,719,670 A | 1/1988 | Kurt |
| 4,719,709 A | 1/1988 | Vaccari |
| 4,761,834 A | 8/1988 | Kolb |
| 4,796,610 A | 1/1989 | Cromartie |
| 4,799,297 A | 1/1989 | Baggio et al. |
| 4,802,291 A | 2/1989 | Sartor |
| 4,805,605 A | 2/1989 | Glassman |
| 4,807,605 A | 2/1989 | Mattingly |
| 4,811,503 A | 3/1989 | Iwama |
| 4,843,688 A | 7/1989 | Ikeda |
| 4,862,878 A | 9/1989 | Davison et al. |
| 4,870,761 A | 10/1989 | Tracy |
| 4,905,678 A | 3/1990 | Cumins et al. |
| 4,923,474 A | 5/1990 | Klasson et al. |
| 4,937,952 A | 7/1990 | Olivieri |
| 4,961,544 A | 10/1990 | Bidoia |
| 4,963,208 A | 10/1990 | Muncy et al. |
| 4,976,257 A | 12/1990 | Akin et al. |
| 5,027,482 A | 7/1991 | Torppey |
| 5,072,725 A | 12/1991 | Miller |
| 5,074,288 A | 12/1991 | Miller |
| 5,092,321 A | 3/1992 | Spademan |
| 5,098,770 A | 3/1992 | Paire |
| 5,105,828 A | 4/1992 | Grant |
| 5,111,807 A | 5/1992 | Spahn et al. |
| 5,120,288 A | 6/1992 | Sinaki |
| 5,121,741 A | 6/1992 | Bremer et al. |
| 5,127,897 A | 7/1992 | Roller |
| 5,135,470 A | 8/1992 | Reeves |
| 5,135,471 A | 8/1992 | Houswerth |
| 5,154,690 A | 10/1992 | Shiono |
| 5,157,813 A | 10/1992 | Carroll |
| 5,170,505 A | 12/1992 | Rohrer |
| 5,171,296 A | 12/1992 | Herman |
| 5,176,131 A | 1/1993 | Votel et al. |
| 5,177,882 A | 1/1993 | Berger |
| 5,181,331 A | 1/1993 | Berger |
| 5,183,036 A | 2/1993 | Spademan |
| D334,063 S | 3/1993 | DeWall |

(56) References Cited

U.S. PATENT DOCUMENTS

| | | |
|---|---|---|
| 5,199,940 A | 4/1993 | Morris et al. |
| 5,201,074 A | 4/1993 | Dicker |
| 5,203,765 A | 4/1993 | Friddle, Jr. |
| 5,215,518 A | 6/1993 | Rosen |
| 5,226,874 A | 7/1993 | Heinz et al. |
| 5,230,698 A | 7/1993 | Garth |
| 5,259,831 A | 11/1993 | LeBron |
| 5,259,833 A | 11/1993 | Barnett |
| 5,295,947 A | 3/1994 | Muncy |
| 5,307,521 A | 5/1994 | Davis |
| 5,313,952 A | 5/1994 | Hoch |
| 5,318,575 A | 6/1994 | Chesterfield et al. |
| 5,327,662 A | 7/1994 | Hallenbeck |
| 5,334,135 A | 8/1994 | Grim et al. |
| 5,342,289 A | 8/1994 | Munny |
| 5,346,461 A | 9/1994 | Heinz et al. |
| 5,363,863 A | 11/1994 | Lelli et al. |
| 5,365,947 A | 11/1994 | Bonutti |
| 5,368,552 A | 11/1994 | Williamson et al. |
| 5,376,129 A | 12/1994 | Faulkner et al. |
| 5,383,893 A | 1/1995 | Daneshvar |
| 5,387,245 A | 2/1995 | Fay et al. |
| 5,399,151 A | 3/1995 | Smith |
| 5,421,809 A | 6/1995 | Rise |
| 5,423,852 A | 6/1995 | Daneshvar |
| 5,429,587 A | 7/1995 | Gates |
| 5,433,648 A | 7/1995 | Frydman |
| 5,433,697 A | 7/1995 | Cox |
| 5,435,015 A | 7/1995 | Ellis-Brewer |
| 5,437,614 A | 8/1995 | Grim |
| 5,437,617 A | 8/1995 | Heinz et al. |
| 5,437,619 A | 8/1995 | Malewicz et al. |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | DeRoche |
| 5,499,965 A | 3/1996 | Sanchez |
| 5,500,959 A | 3/1996 | Yewer, Jr. |
| 5,502,902 A | 4/1996 | Sussmann |
| 5,503,314 A | 4/1996 | Fiscus |
| 5,503,620 A | 4/1996 | Danzger |
| 5,507,681 A | 4/1996 | Smith et al. |
| 5,507,834 A | 4/1996 | Laghi |
| 5,520,619 A | 5/1996 | Martin |
| 5,522,792 A | 6/1996 | Bassett et al. |
| 5,531,669 A | 7/1996 | Varnau |
| 5,536,246 A | 7/1996 | Saunders |
| 5,539,020 A | 7/1996 | Bracken et al. |
| 5,548,843 A | 8/1996 | Chase et al. |
| 5,551,950 A | 9/1996 | Oppen |
| 5,558,628 A | 9/1996 | Bzoch |
| 5,569,171 A | 10/1996 | Muncy |
| 5,571,355 A | 11/1996 | Kornylo |
| 5,599,287 A | 2/1997 | Beczak, Sr. et al. |
| 5,599,288 A | 2/1997 | Shirley et al. |
| 5,603,122 A | 2/1997 | Kania |
| 5,620,412 A | 4/1997 | Modglin |
| 5,622,529 A | 4/1997 | Calabrese |
| 5,632,724 A | 5/1997 | Lerman et al. |
| 5,634,891 A | 6/1997 | Beczak, Sr. et al. |
| 5,638,588 A | 6/1997 | Jungkind |
| 5,669,116 A | 9/1997 | Jungkind |
| 5,674,187 A | 10/1997 | Zepf |
| 5,681,270 A | 10/1997 | Klearman et al. |
| 5,685,830 A | 11/1997 | Bonutti |
| 5,685,831 A | 11/1997 | Floyd |
| 5,688,137 A | 11/1997 | Bustance |
| 5,690,260 A | 11/1997 | Aikins et al. |
| 5,690,609 A | 11/1997 | Heinze, III |
| 5,695,452 A | 12/1997 | Grim et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,722,940 A | 3/1998 | Gaylord, Jr. et al. |
| 5,724,993 A | 3/1998 | Dunfee |
| 5,725,139 A | 3/1998 | Smith |
| 5,728,054 A | 3/1998 | Martin |
| 5,728,168 A | 3/1998 | Laghi et al. |
| 5,732,483 A | 3/1998 | Cagliari |
| 5,737,854 A | 4/1998 | Sussmann |
| 5,746,218 A | 5/1998 | Edge |
| 5,752,640 A | 5/1998 | Prouix |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,819,378 A | 10/1998 | Doyle |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,848,979 A | 12/1998 | Bonutti et al. |
| 5,853,378 A | 12/1998 | Modglin |
| 5,853,379 A | 12/1998 | Ostojic |
| 5,857,988 A | 1/1999 | Shirley |
| 5,868,292 A | 2/1999 | Stephens et al. |
| 5,890,640 A | 4/1999 | Thompson |
| 5,891,061 A | 4/1999 | Kaiser |
| 5,911,697 A | 6/1999 | Biedermann et al. |
| 5,916,070 A | 6/1999 | Donohue |
| 5,938,629 A | 8/1999 | Bloedau |
| 5,950,628 A | 9/1999 | Dunfee |
| 5,954,250 A | 9/1999 | Hall et al. |
| 5,954,253 A | 9/1999 | Swetish |
| 5,967,998 A | 10/1999 | Modglin |
| 5,993,403 A | 11/1999 | Martin |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin, Sr. et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A | 8/2000 | Turtzo |
| 6,110,138 A | 8/2000 | Shirley |
| 6,117,096 A | 9/2000 | Hassard |
| RE36,905 E | 10/2000 | Noble et al. |
| 6,125,792 A | 10/2000 | Gee |
| 6,129,638 A | 10/2000 | Davis |
| 6,129,691 A | 10/2000 | Ruppert |
| 6,156,001 A | 12/2000 | Frangi et al. |
| 6,159,248 A | 12/2000 | Gramnas |
| 6,182,288 B1 | 2/2001 | Kibbee |
| 6,190,343 B1 | 2/2001 | Heinz et al. |
| D438,624 S | 3/2001 | Reina |
| 6,206,932 B1 | 3/2001 | Johnson |
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,256,798 B1 | 7/2001 | Egolf et al. |
| 6,267,390 B1 | 7/2001 | Maravetz et al. |
| 6,282,729 B1 | 9/2001 | Oikawa et al. |
| 6,289,558 B1 | 9/2001 | Hammerslag |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,401,786 B1 | 6/2002 | Tedeschi et al. |
| 6,413,232 B1 | 7/2002 | Townsend et al. |
| 6,416,074 B1 | 7/2002 | Maravetz et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,502,577 B1 | 1/2003 | Bonutti |

(56) References Cited

U.S. PATENT DOCUMENTS

| | | |
|---|---|---|
| 6,503,213 B2 | 1/2003 | Bonutti |
| 6,517,502 B2 | 2/2003 | Heyman et al. |
| 6,540,703 B1 | 4/2003 | Lerman |
| 6,589,195 B1 | 7/2003 | Schwenn et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 | 9/2003 | Smith et al. |
| 6,652,596 B2 | 11/2003 | Smith et al. |
| 6,676,617 B1 | 1/2004 | Miller |
| 6,676,620 B2 | 1/2004 | Schwenn et al. |
| 6,688,943 B2 | 2/2004 | Nagaoka |
| 6,689,080 B2 | 2/2004 | Castillo |
| 6,702,770 B2 | 3/2004 | Bremer et al. |
| 6,711,787 B2 | 3/2004 | Jungkind et al. |
| 6,726,643 B1 | 4/2004 | Martin |
| 6,769,155 B2 | 8/2004 | Hess et al. |
| 6,770,047 B2 | 8/2004 | Bonutti |
| 6,790,191 B1 | 9/2004 | Hendricks |
| 6,802,442 B1 | 10/2004 | Thompson |
| D499,806 S | 12/2004 | Machin et al. |
| D501,078 S | 1/2005 | Cabana |
| 6,893,098 B2 | 5/2005 | Kohani |
| 6,893,411 B1 | 5/2005 | Modglin |
| 6,913,585 B2 | 7/2005 | Salmon et al. |
| 6,921,375 B2 | 7/2005 | Kihara |
| 6,921,377 B2 | 7/2005 | Bonutti |
| 6,923,780 B2 | 8/2005 | Price et al. |
| 6,926,685 B1 | 8/2005 | Modglin |
| 6,936,021 B1 | 8/2005 | Smith |
| 6,942,630 B2 | 9/2005 | Behan |
| 6,951,547 B1 | 10/2005 | Park et al. |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,034,251 B1 | 4/2006 | Child et al. |
| 7,048,707 B2 | 5/2006 | Schwenn et al. |
| 7,074,204 B2 | 7/2006 | Fujii et al. |
| 7,083,584 B2 | 8/2006 | Coligado |
| 7,083,585 B2 | 8/2006 | Latham |
| 7,087,032 B1 | 8/2006 | Ikeda |
| 7,101,348 B2 | 9/2006 | Garth et al. |
| 7,118,543 B2 | 10/2006 | Telles et al. |
| 7,128,724 B2 | 10/2006 | Marsh |
| 7,134,224 B2 | 11/2006 | Elkington et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,198,610 B2 | 4/2007 | Ingimundarson et al. |
| 7,201,727 B2 | 4/2007 | Schwenn et al. |
| 7,235,059 B2 | 6/2007 | Mason et al. |
| 7,281,341 B2 | 10/2007 | Reagan et al. |
| 7,306,571 B2 | 12/2007 | Schwenn et al. |
| 7,306,573 B2 | 12/2007 | Bonutti |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,331,126 B2 | 2/2008 | Johnson |
| 7,351,368 B2 | 4/2008 | Abrams |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,473,235 B2 | 1/2009 | Schwenn et al. |
| 7,476,185 B2 | 1/2009 | Drennan |
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt, III et al. |
| 7,618,386 B2 | 11/2009 | Nordt, III et al. |
| 7,618,389 B2 | 11/2009 | Nordt, III et al. |
| 7,654,972 B2 | 2/2010 | Alleyne |
| 7,662,121 B2 | 2/2010 | Zours |
| 7,670,306 B2 | 3/2010 | Nordt, III et al. |
| 7,682,219 B2 | 3/2010 | Falla |
| 7,699,797 B2 | 4/2010 | Nordt, III et al. |
| 7,704,219 B2 | 4/2010 | Nordt, III et al. |
| 7,727,048 B2 | 6/2010 | Gransberry |
| 7,727,174 B2 | 6/2010 | Chang et al. |
| 7,775,999 B2 | 8/2010 | Brown |
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,857,776 B2 | 12/2010 | Frisbie |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt, III et al. |
| 7,887,500 B2 | 2/2011 | Nordt, III et al. |
| 7,914,473 B2 | 3/2011 | Josey |
| D636,494 S | 4/2011 | Garth et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,959,591 B2 | 6/2011 | Powers et al. |
| 7,993,296 B2 | 8/2011 | Nordt, Iii et al. |
| 8,002,724 B2 | 8/2011 | Hu et al. |
| 8,006,877 B2 | 8/2011 | Lowry et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,308,869 B2 | 11/2012 | Gardner et al. |
| 8,372,023 B2 | 2/2013 | Garth et al. |
| 8,556,840 B2 | 10/2013 | Burke et al. |
| 8,597,222 B2 | 12/2013 | Lucero et al. |
| 8,795,215 B2 | 8/2014 | Rossi |
| 8,956,315 B2 | 2/2015 | Garth et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2003/0000986 A1 | 1/2003 | Smith |
| 2003/0028952 A1 | 2/2003 | Fujii et al. .......... 342/423 |
| 2003/0125650 A1 | 7/2003 | Grosso |
| 2003/0125705 A1 | 7/2003 | Ruman et al. |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |

(56) References Cited

U.S. PATENT DOCUMENTS

| | | |
|---|---|---|
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1 | 6/2006 | Ingimundarson et al. |
| 2006/0155229 A1 | 7/2006 | Ceriani et al. |
| 2006/0156517 A1 | 7/2006 | Hammerslag et al. |
| 2006/0206992 A1 | 9/2006 | Godshaw et al. |
| 2007/0152007 A1 | 7/2007 | Kauss et al. |
| 2007/0167895 A1 | 7/2007 | Gramza et al. |
| 2007/0179417 A1 | 8/2007 | Schwenn et al. |
| 2007/0185425 A1 | 8/2007 | Einarsson et al. |
| 2008/0045873 A1* | 2/2008 | Zours ................ A61F 5/026 602/19 |
| 2008/0091132 A1 | 4/2008 | Bonutti |
| 2008/0195010 A1 | 8/2008 | Lai et al. |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1 | 7/2009 | Grim et al. |
| 2009/0192425 A1 | 7/2009 | Garth et al. |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0139057 A1 | 6/2010 | Soderberg et al. |
| 2010/0204630 A1* | 8/2010 | Sandifer ............ A61F 5/026 602/19 |
| 2010/0217167 A1 | 8/2010 | Ingimundarson et al. |
| 2010/0256717 A1 | 10/2010 | Brown |
| 2010/0268139 A1 | 10/2010 | Garth |
| 2010/0268141 A1 | 10/2010 | Bannister |
| 2010/0274364 A1 | 10/2010 | Pacanowsky et al. |
| 2010/0299959 A1 | 12/2010 | Hammerslag et al. |
| 2010/0318010 A1* | 12/2010 | Sandifer ............ A61F 5/026 602/19 |
| 2011/0000005 A1 | 1/2011 | Brown |
| 2011/0009793 A1 | 1/2011 | Lucero et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0137221 A1 | 6/2011 | Brown |
| 2011/0144551 A1 | 6/2011 | Johnson |
| 2011/0152737 A1 | 6/2011 | Burke et al. |
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2012/0010547 A1 | 1/2012 | Hinds |
| 2012/0022420 A1 | 1/2012 | Sandifer et al. |
| 2012/0029404 A1 | 2/2012 | Weaver, II et al. |
| 2012/0197167 A1 | 8/2012 | Kruijsen et al. |
| 2012/0204381 A1 | 8/2012 | Ingimundarson et al. |
| 2012/0232450 A1 | 9/2012 | Garth et al. |
| 2012/0323154 A1 | 12/2012 | Ingimundarson et al. |
| 2013/0006158 A1 | 1/2013 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0184628 A1 | 7/2013 | Ingimundarson et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |
| 2013/0298914 A1 | 11/2013 | Shibaya et al. |
| 2014/0200121 A1 | 7/2014 | Von Hoffmann et al. |
| 2014/0336020 A1 | 11/2014 | Von Hoffmann et al. |

FOREIGN PATENT DOCUMENTS

| | | |
|---|---|---|
| AU | 2010286851 A1 | 3/2012 |
| AU | 2010286851 A2 | 5/2012 |
| CA | 2 112 789 A1 | 8/1994 |
| CA | 2 114 387 A1 | 8/1994 |
| CA | 2767353 A1 | 1/2011 |
| CA | 2772296 A1 | 3/2011 |
| CH | 577 282 A5 | 7/1976 |
| CH | 612 076 A5 | 7/1979 |
| CH | 624 001 A5 | 7/1981 |
| CN | 1311648 A | 9/2001 |
| CN | 201101603 Y | 8/2008 |
| CN | 102470040 A | 5/2012 |
| DE | 1197192 B | 7/1965 |
| DE | 8804683 U1 | 6/1988 |
| DE | 38 22 113 A1 | 1/1990 |
| DE | 93 15 776 U1 | 2/1995 |
| DE | 295 03 552 U1 | 4/1995 |
| DE | 199 45 045 A1 | 3/2001 |
| DE | 20204747 U1 | 7/2002 |
| DE | 10329454 | 1/2005 |
| DE | 202004015328 U1 | 2/2005 |
| DE | 202005007124 U1 | 6/2005 |
| DE | 20 2009 004 817 U1 | 9/2010 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0657149 A1 | 6/1995 |
| EP | 0 589 232 B1 | 11/1995 |
| EP | 0 693 260 B1 | 9/1998 |
| EP | 0 651 954 B1 | 2/1999 |
| EP | 1159940 A2 | 12/2001 |
| EP | 1 236 412 A1 | 9/2002 |
| EP | 1 342 423 A1 | 9/2003 |
| EP | 1588678 A1 | 10/2005 |
| EP | 1743608 | 1/2007 |
| EP | 1985264 | 4/2008 |
| EP | 2200545 A1 | 6/2010 |
| EP | 2451412 A1 | 5/2012 |
| EP | 2473072 A1 | 7/2012 |
| FR | 1104562 A | 11/1955 |
| FR | 2 757 073 A1 | 6/1998 |
| FR | 2952807 A1 | 5/2011 |
| GB | 826 041 A | 12/1959 |
| GB | 909970 A | 11/1962 |
| GB | 2133289 A | 7/1984 |
| JP | 3031760 U | 12/1996 |
| JP | H09-273582 A | 10/1997 |
| JP | H10-237708 A | 9/1998 |
| JP | 2000-290331 A | 10/2000 |
| JP | 2001204851 A | 7/2001 |
| JP | 2003-175063 A | 6/2003 |
| JP | 2004-016732 A | 1/2004 |
| JP | 2004-041666 A | 2/2004 |
| JP | 2004209050 A | 7/2004 |
| JP | 2007-291536 A | 11/2007 |
| JP | 3142546 U | 6/2008 |

(56) References Cited

FOREIGN PATENT DOCUMENTS

| | | | |
|---|---|---|---|
| JP | 2009-082697 | A | 4/2009 |
| JP | 2012011550 | A | 1/2012 |
| JP | 2013503268 | A | 1/2013 |
| JP | 2013536010 | A | 9/2013 |
| WO | 94/01496 | A1 | 1/1994 |
| WO | 95/03720 | A2 | 2/1995 |
| WO | 97/03581 | A1 | 2/1997 |
| WO | 00/53045 | A1 | 9/2000 |
| WO | 2004/110197 | A2 | 12/2004 |
| WO | 2005086752 | A2 | 9/2005 |
| WO | 2005086752 | A3 | 9/2005 |
| WO | 2006121413 | | 11/2006 |
| WO | 2009017499 | | 2/2009 |
| WO | 2009017949 | | 2/2009 |
| WO | 2009052031 | | 4/2009 |
| WO | 2009068503 | A1 | 6/2009 |
| WO | 2011005430 | A1 | 1/2011 |
| WO | 2011025675 | A1 | 3/2011 |
| WO | 2011/066323 | A1 | 6/2011 |
| WO | 2012/029917 | A1 | 3/2012 |
| WO | 2013016670 | A1 | 1/2013 |

OTHER PUBLICATIONS

International Search Report from International PCT Application No. PCT/US98/08975, Jul. 8, 1998.
Supplemental EP Search Report from EP Application No. 98920943, Dec. 7, 2004.
International Search Report from PCT Application No. PCT/JP2011/069929, dated Oct. 18, 2011.
International Search Report from International PCT Application No. PCT/US2014/012860, Apr. 17, 2014.
Examination report from EP Application No. 12740242.8, Sep. 3, 2015.
Pamphlet—"Bledsoe Phillippon K.A.F. Positioning Kit, Application Instructions (CP020205 Rev B Apr. 2007), New Hip Arthroscopy Padding and Positioning Kit", Council Directive 93/42/EEC of Jun. 14, 1993 concerning Medical Devices, 2 pages.
Pamphlet—"Bledsoe Phillippon K.A.F. Positioning Kit", Bledsoe Brace Systems, Medical Technology Inc., 2004, 2 pages.
Hsu et al., "Principles and Components of Spinal Orthoses", AAOS Atlas of Orthoses and Assistive Devices, 4th Ed., Chpater 7, 2008, pp. 89-111.
Written Opinion of the International Searching Authority Corresponding to International Application No. PCT/US2010/002893.
International Search Report Corresponding to PCT Application No. PCT/US2010/000601, Jun. 28, 2010.
International Search Report Corresponding to International Application No. PCT/US2010/002893 dated Feb. 22, 2011.
International Preliminary Report of Patentability from PCT Application No. PCT/US2010/000601, Aug. 30, 2011.
Bledsoe Products, "Philippon K.A.F. Positioning Kit". http://bledsoebrace.com/products/kaf.asp [retrieved from internet May 10, 2012].
International Search Report and Written Opinion Issued in PCT/US2012/024619, May 16, 2012.
International Search Report and Written Opinion of the International Searching Authority Issued in PCT/US2012/043252, Jan. 10, 2013.
Sato, Ena et al., "Effect of the WISH-type hip brace on functional mobility in patients with osteoarthritis of the hip: evaluation using the time UP & GO", Prosthetics and Orthotics International 2012 36:25 originally published online Nov. 17, 2011, http://poi.sagepub.com/content/36/125 [retrieved from internet on Jan. 22, 2014].
Charles T. Mehlman, John P. Schwegmann; Hyphenated History:Knight-Taylor Spinal Orthosis; American Journal of Orthopedics; Jun. 2000; pp. 479-483, vol. 29, Issue 6.
http://www.flaorthopedics.com; Posture Control Brace; 2004; FLA Orthopedics, Inc.
http://www.scoliosisspecialists.com/aboutspinecorbrace.html;
About the SpineCor Brace; 2006-2012; Scoliosis Specialists.
International Search Report from corresponding PCT Application No. PCT/US2013/021170 dated Apr. 12, 2013.
Spinomed® brochure-Spinal Orthosis for Vertebral Extension in Osteoporosis, Stellar Orthotics and Prosthetics Group, retrieved from Internet Sep. 23, 2013. http://stellaroandp.com/spotlight.html.
Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.
International Search Report from Corresponding PCT Application No. PCT/US2013/066425 dated Mar. 18, 2014.

\* cited by examiner

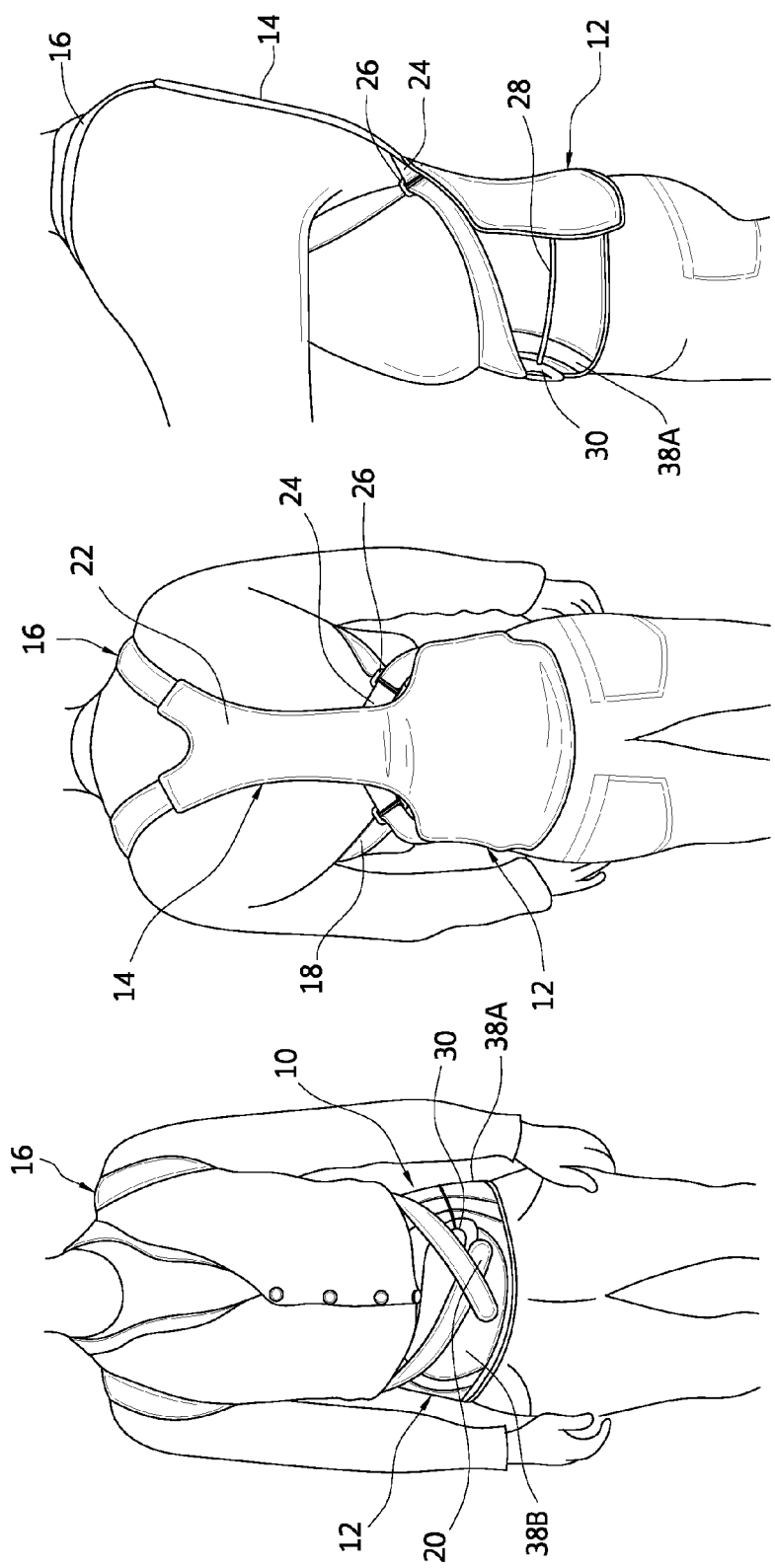

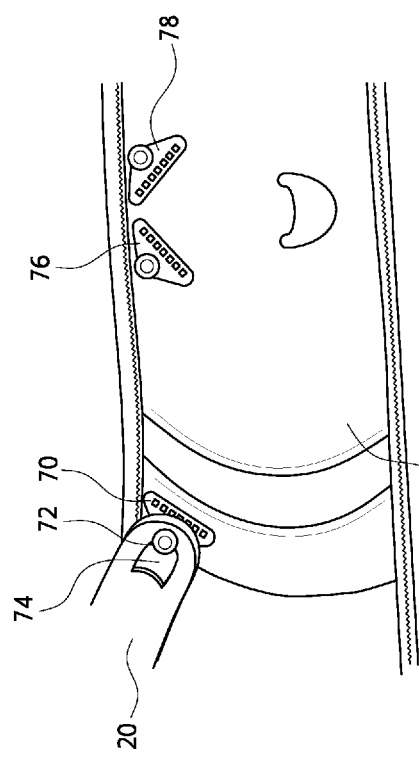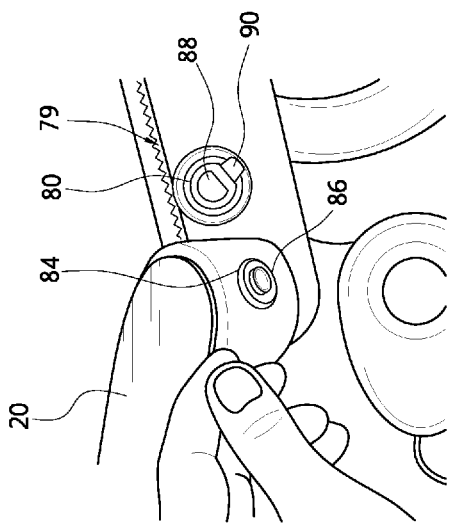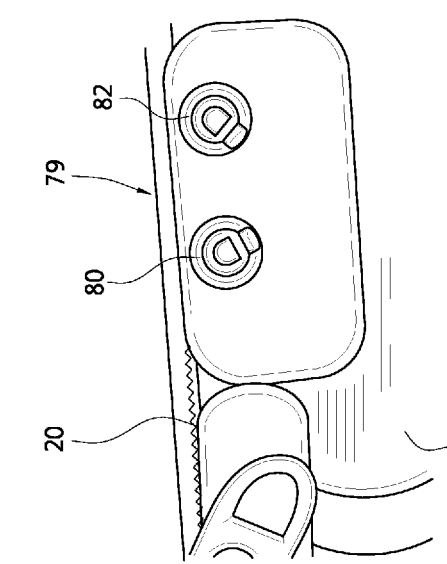

SPINAL ORTHOSIS

FIELD OF THE INVENTION

The invention relates to an orthopedic device, and more particularly to a spinal orthosis for providing corrective assistance to a spinal column.

BACKGROUND

Many osteoporosis related fractures occur in the wrist, spine, or hip. Bones become weak due to osteoporosis and require support when healing from a fracture. The incidence of these fractures caused by osteoporosis, particularly vertebral, is rapidly rising with aging in both sexes.

Regarding spinal or vertebral osteoporosis, it is believed that a fourth of women 50 years of age in the general population have one or more vertebral fractures resulting in loss of height and increased kyphosis. Kyphotic postural change is the most physically disfiguring and psychologically damaging effect of osteoporosis and can contribute to an increase in vertebral fractures and risk of falling. Spinal osteoporosis may be associated with reduced pulmonary function, chronic pain, limitations in everyday life, and emotional problems related to appearance.

Therapeutic interventions with proven efficacy include alendronate, risedronate, and raloxifene, which improve bone quality. These therapeutics, however, only prevent approximately 50% of spinal fractures. There is a need to improve back muscle strength because muscle atrophy parallels the decline of bone mineral density of the spine and contributes significantly to kyphotic postural changes. The multi-disciplinary rehabilitation concept of spinal osteoporosis includes back-strengthening exercises to counteract thoracic kyphosis in hyperkyphotic subjects Using a spinal orthosis can increase trunk muscle strength and improve posture in individuals with vertebral fractures caused by osteoporosis. Wearing a spinal orthosis can lead to a better quality-of-life by pain reduction, decreased limitations of daily living, and an improvement of well-being. Use of an orthosis may represent an efficacious nonpharmacologic treatment option for spinal osteoporosis. Indications for a spinal orthosis include osteoporosis inclusive of acute and chronic pain due to osteoporosis, hyperkyphosis, compression fracture, pain relieved by thoracic extension, spinal stenosis, post-operative support, and vertebral collapse Traditionally, spinal orthoses have been used in the management of thoracolumbar injuries treated with or without surgical stabilization. The vast majority of orthoses, however, are used in individuals with low back pain. In the United States alone, nearly 250,000 corsets are prescribed each year.

The orthotic treatment modality in the management of vertebral fractures caused by osteoporosis revolves around keeping the spinal column extended to relieve the pressure on the anterior side of the vertebrae, which is the most common area of fracture. This can be done through compression of the lumbar spine with a corset having an anterior panel for intracavitary compression, a posterior panel that extends over the shoulders and auxiliary straps that come across the chest to pull the upper back into extension. There are challenges with these designs in that they are found to be bulky and difficult to don and doff, and often fail to provide the correct tension. It is perceived by many that long term immobilization of such devices can have a negative effect on back extensor strength essential to long term outcomes for such individuals.

Orthoses may be used for treating various spinal deformities, including scoliotic and kyphotic deformities. Scoliosis occurs when there is lateral curvature of the spine above a certain degree. Lateral curvature is typically associated with vertebral rotation within the curve in which three-dimensional deformity results.

Many types of orthoses exist for treating scoliosis. Many of these orthoses are arranged to create a foundation by grasping a pelvis and include a metal suprastructure over the torso to create a rigid framework upon which a series of inelastic straps and pads are arranged to provide corrective force to the spinal deformity. A goal behind the braces is to apply corrective forces at the deformity in a manner to allow the torso and spine to shift in a normal position.

SUMMARY

The spinal orthosis embodiments of this disclosure are provided to reduce loads on a vertebra or vertebrae in acute and chronic phases to minimize pain and increase mobility of the individual by reducing functional disability.

The embodiments offer a comfortable and low profile lumbar assembly providing efficient compression around the lumbar area in combination with a rigid posterior frame assembly extending along the spine while securing to the lumbar brace and connecting to a strapping system extending over the shoulders and securing to the lumbar assembly. The strapping system of the spinal orthosis is intended for uncomplicated and effortless use for the wearer and enables the chest to be pulled into extension while counteracting with the posterior spinal frame. The spinal orthosis provides a system for consistent donning and immobilization that allows the wearer to use the spinal orthosis in a prescribed manner under the dictates of a practitioner and despite physical limitations of the wearer.

By providing wearer comfort and means for encouraging wearer compliance for wearing the spinal orthosis, the spinal orthosis provides functional relief of vertebral fracture pain, and facilitates a return to mobility. Particularly, while not limited to such treatment, the spinal orthosis is aimed at reducing pain and improving function in individuals with vertebral fractures from L5 (lumbar vertebrae) to T4 (thoracic vertebrae).

In embodiment used to treat scoliosis, a spinal orthosis has an elongate and substantially rigid spinal frame having upper, middle and lower portions, and a lumbar assembly connected to the lower portion of the spinal frame. A strap assembly includes at least one strap having a first end secured to the upper portion of the spinal frame and a second end adjustably securing to the lumbar assembly. An elastic strap has a first end secured to the spinal frame and a second end adjustably securing to the lumbar assembly.

The elastic band is arranged to resist movement by stretching and resisting movement to pull the spine into a corrective position. The spinal frame serves as a foundation for the elastic strap and is positionable over a plurality of locations over the lumbar assembly to allow for a desirable and comfortable orientation.

A method for using the spinal orthosis includes anchoring a first end of the elastic strap along the spinal orthosis and anchoring a second end of the elastic strap to the lumbar assembly. The elastic strap may be secured along either first or second lateral sides of the spinal frame, along a plurality of heights along the spinal frame, and secured to a plurality of locations along the lumbar assembly.

BRIEF DESCRIPTION OF THE DRAWINGS

These and other features, aspects, and advantages of the present invention will become better understood regarding the following description, appended claims, and accompanying drawings.

FIG. 1 is a front view of an embodiment of a spinal orthosis on a wearer.

FIG. 2 is a rear view of the spinal orthosis embodiment of FIG. 1.

FIG. 3 is a side view of the spinal orthosis embodiment of FIG. 1.

FIG. 23 is a schematic view of attachment points for the strap assembly on the belt segments of the lumbar assembly.

FIG. 25 is a schematic view of a variation of a consistent donning system in an open configuration.

FIG. 26 is a schematic view of the donning system of FIG. 25 when adjusting the brace.

Figure 4A:
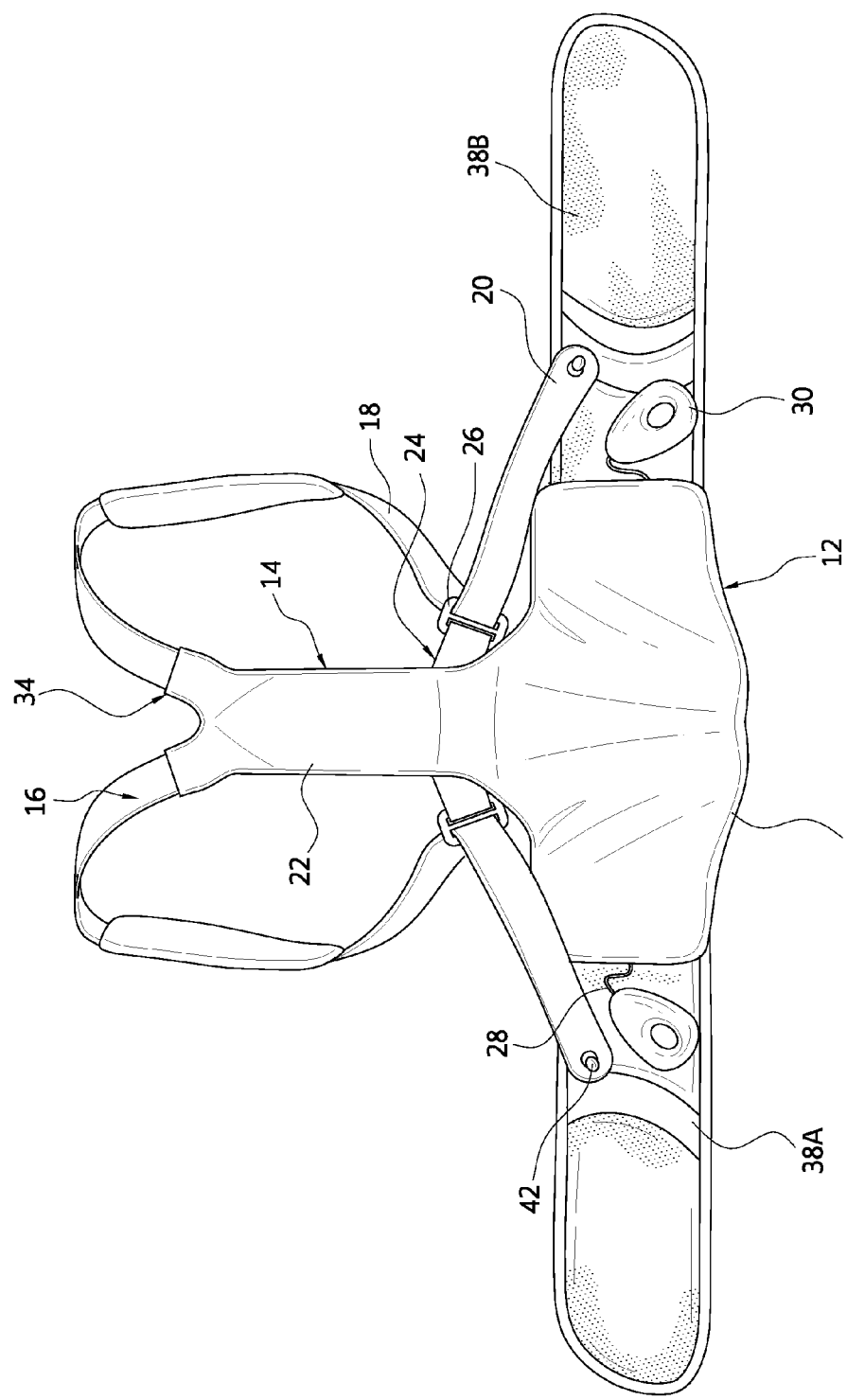
FIG. 4A is an exterior elevational view of a variation of the spinal orthosis of FIG. 1.

The drawing figures are not necessarily drawn to scale, but instead are drawn to provide a better understanding of the components, and are not intended to be limiting in scope, but rather to provide exemplary illustrations. The figures illustrate exemplary configurations of a spinal orthosis having height and circumferential adjustment and the respective components, and in no way limit the structures or configurations of the spinal orthosis and components according to the present disclosure.

DETAILED DESCRIPTION OF VARIOUS EMBODIMENTS

A. Overview

A better understanding of different embodiments of the invention may be had from the following description read with the accompanying drawings in which like reference characters refer to like elements.

While the disclosure is susceptible to various modifications and alternative constructions, certain illustrative embodiments are in the drawings and are described below in detail. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of an orthopedic device in the exemplary form of a spinal orthosis and variants as disclosed, a description of a few terms is necessary. As used, the term "proximal" has its ordinary meaning and refers to a location situated next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Last, the term "anterior" has its ordinary meaning and refers to a location ahead of or to the front of another location.

The terms "rigid," "flexible," "compliant," and "resilient" may be used to distinguish characteristics of portions of certain features of the orthopedic device. The term "rigid" should denote that an element of the device is generally devoid of flexibility. Within the context of features that are "rigid," it is intended to indicate that they do not lose their overall shape when force is applied, and may break if bent with sufficient force. The term "flexible" should denote that features are capable of repeated bending such that the features may be bent into retained shapes or the features do not retain a general shape, but continuously deform when force is applied.

The term "compliant" may qualify such flexible features as generally conforming to the shape of another object when placed in contact therewith, via any suitable natural or applied forces, such as gravitational forces, or forces applied by external mechanisms, for example, strap mechanisms. The term "resilient" may qualify such flexible features as generally returning to an initial general shape without permanent deformation. As for the term "semi-rigid," this term may be used to connote properties of support members or shells that provide support and are free-standing; however such support members or shells may have some degree of flexibility or resiliency.

The embodiments of the disclosure are adapted for a human body, and may be dimensioned to accommodate different types, shapes and sizes of human body sizes and contours. For explanatory purposes, the orthosis embodiments described are referred to as corresponding to different sections of a body and are denoted by general anatomical terms for the human body.

The embodiments of the orthosis are particularly referred to as corresponding to anterior and posterior body sections by an anterior-posterior plane. The anatomical terms described are not intended to detract from the normal understanding of such terms as readily understood by one of ordinary skill in the art of orthopedics.

B. Various Embodiments of the Orthopedic Device and Components for Use Therewith Under the embodiment in FIGS. 1-5, an orthopedic device in the exemplary form of a spinal orthosis 10 is provided, among other functions, for increasing trunk muscle strength and improving posture in individuals with vertebral fractures.

The orthosis 10 includes a lumbar assembly 12, a posterior frame assembly or spinal frame 14, and a strap assembly 16. The strap assembly 16 includes elongate straps 18 that engage an upper portion of the spinal frame 14 near or at the posterior shoulders and extend over the shoulders and under the armpits to orient a middle bracket assembly 24 on a middle portion of the spinal frame 14. The straps 18 are redirected by brackets 26 carried by the middle bracket assembly 24 toward the anterior side of the lumbar assembly 12 whereat the strap ends 20 secure to the surface of the lumbar assembly 12.

The strap assembly 16 permits downward pulling of the straps at a location, such as the waist or abdomen, which is easier for a geriatric individual to pull than at the shoulders, as in many prior art orthoses. Wearers of the orthosis that are arthritic or have poor dexterity need only pull down the straps at a location roughly below the chest to tighten the strap assembly over the shoulders. They may similarly attach the strap ends to the lumbar support at a relatively low location that is comfortable and easy for the wearer to manipulate.

Both the closure system of the lumbar assembly 12 and the spinal frame 14 may be covered by suitable sleeves or covers 22, 46 to cushion and conceal these various features, leading to an aesthetically pleasing and comfortable arrangement. The lumbar assembly 12 includes first and second belt segments 38A, 38B (collectively 38) which permit easy donning of the assembly over the waist. Suitable additional padding may be provided along the strap assembly, for example over the shoulders to provide compressive relief to the wearer when the strap assembly is tensioned, or along the spinal frame and lumbar assembly.

Figure 4B:
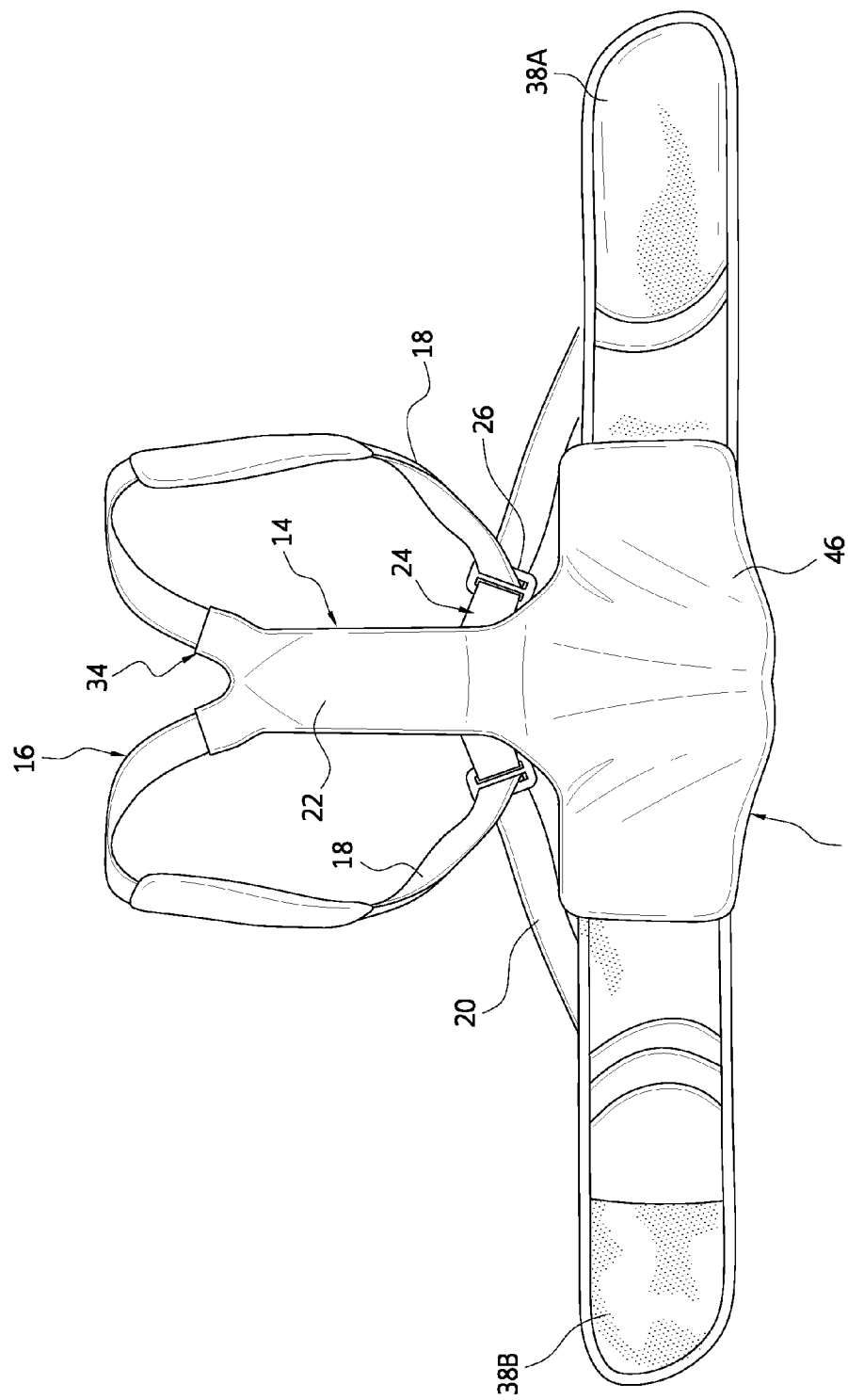
FIG. 4B is an interior elevational view of the spinal orthosis of FIG. 4A.

When assembling the spinal orthosis on a wearer, as shown in FIGS. 1-3 under the orthosis in FIGS. 4A and 4B, the wearer is preferably in a standing position and is encouraged to stand in an upright position. The wearer places the strap assemblies around shoulders similar to a backpack, whereas the strap ends are either freely extending from the middle bracket assembly downwardly toward or unattached to the lumbar support, or the strap ends are placed at temporary attachment points. The lumbar panel is centered on the spine with the bottom of the rigid posterior panel at approximately the sacrococcygeal joint. If the lumbar assembly includes a rigid or semi-rigid anterior panel, the anterior panel should be centered on the abdomen with the bottom edge just above the symphysis pubis while still allowing the individual to sit comfortably.

Figure 5A:
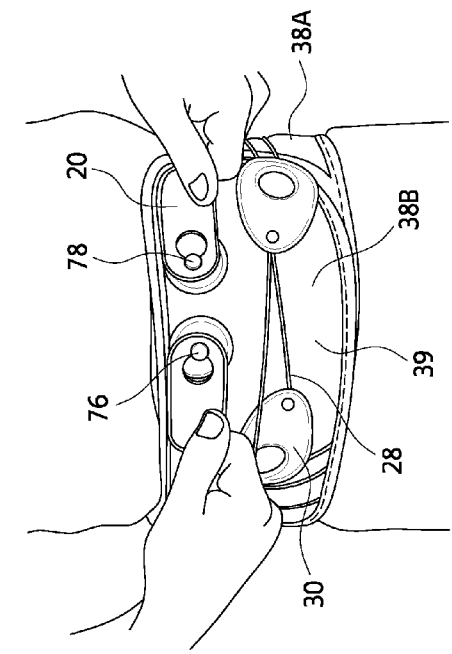
FIGS. 5A-5D show various stages in applying the spinal orthosis and removing the spinal orthosis of FIGS. 4A and 4B.

As shown in FIG. 5A, the belt segments are then secured to one another overlapping one another and wrapping over the abdomen of the wearer. Once the belt segments are secured to the wearer, the wearer simultaneously pulls the handles 30 of the tensioning elements 28 toward the anterior center of the belt segments 38A, 38B and attaches the handles onto the surface of the belt segments when the appropriate tightness is obtained.

Figure 5B:
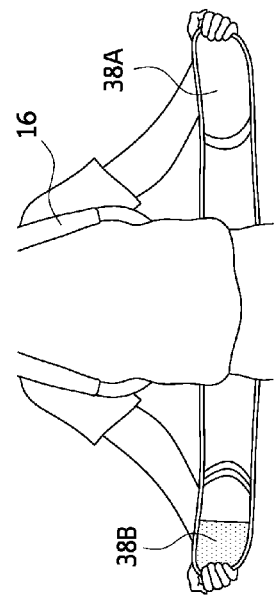

The wearer then removes handles of strap ends 20 of the strap assembly from temporary attachment points or hooks 42 on the left and right sides of the belt segments. The wearer is encouraged to lean into the posterior frame assembly as this makes it easier to tighten the strap assembly. The strap assembly is pulled so that the handles are attached to the belt segments, such as in an overlapping manner as shown in FIG. 1, until a corrective and comfortable amount of compression is obtained in the strap assembly, or attached to attachment points or anterior hooks 76, 78 on the belt segments at predetermined locations as shown in FIG. 5B and FIG. 23.

The bottom edge of the belt segments preferably sit below the hip. The end portion on the belt segment 38B should be centered on the abdomen, and the handles 30 and the strap ends 20 are likewise placed on the end portion. It is preferable that the belt segments grip the waist, and have a higher level of tightness than the shoulder straps.

The tightening of the belt segments induces lordosis in the lower back, which improves the overall posture and reduces the load on the fractured vertebrae. The tightened belt arms also anchor the orthosis properly on the body. The strap assembly pulls the shoulders back without limiting mobility in the shoulder and arm area, and without impairing chest and abdominal breathing. With optimum adjustment, the wearer experiences pain alleviation and increased mobility.

Figure 5C:
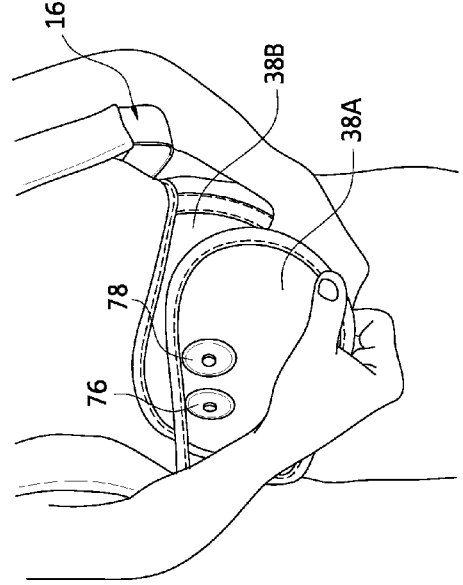
Figure 5D:
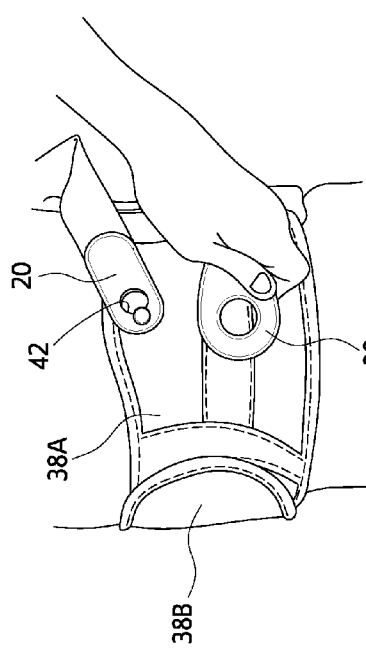

When removing the brace, the strap ends 20 are removed from the hooks 76, 78, and attached to hooks on the sides of the belt segments 38A, 38B, as shown in FIG. 5C. This allows for loosening of the strap system 16. As for the lumbar assembly 12, the handles 30 are adjusted to the sides of the belt segments proximate to the hooks 76, 78 which loosens the tension in the lumbar assembly. The wearer can then freely remove the belt segments 38A, 38B and the strap assembly 16, as shown in FIG. 5D, since all are loosened to the point of brace removal.

Figure 7:
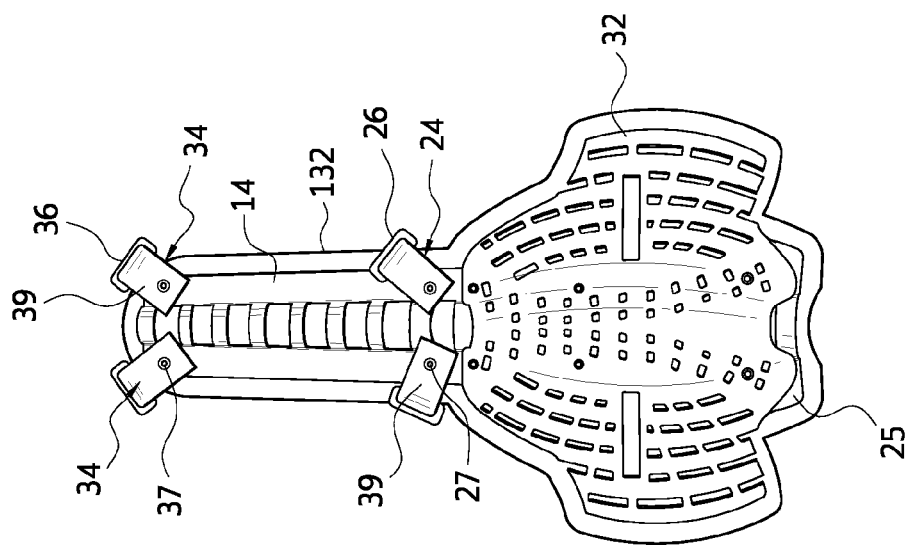
FIG. 7 is an exterior view of the posterior frame assembly and lumbar panel of FIG. 6.
Figure 6:
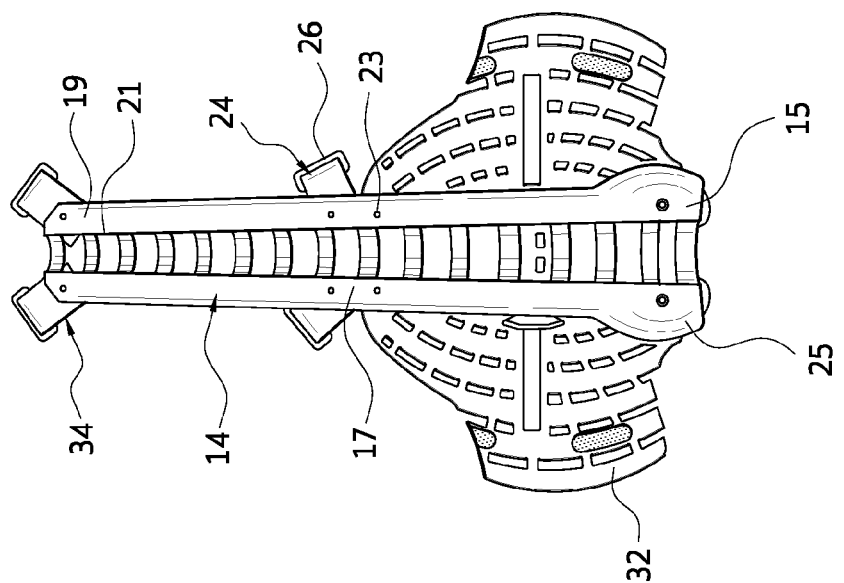
FIG. 6 is an interior view of a posterior frame assembly and lumbar panel in accordance with the spinal orthosis of FIG. 1.

Turning to FIGS. 6 and 7, the posterior frame assembly includes the spinal frame 14 defining an elongate frame having a lower portion 15 corresponding to and extending from a lower portion of a lumbar panel or support 32, such as a flexible or semi-rigid plate or frame, a middle portion 17 located above the lumbar support 32 and carrying the bracket assembly 24, and an upper portion 19 carrying an upper bracket assembly 34. The spinal frame 14 defines a plurality of openings 21 along its length, and is fixedly secured to the lumbar support 32 by a plurality of fasteners 23. The spinal frame 14 may have a profile, as shown, in which the lower portion 15 flares outwardly and the spinal frame narrows in width as it approaches the upper portion 19 to anatomically conform to the wearer's anatomy.

The spinal frame 14 is preferably constructed from a malleable aluminum which can be shaped by a practitioner according to the individual anatomy of a wearer. The lumbar panel of the lumbar assembly may be formed from a plastic that is flexible relative to the spinal frame. Lateral side portions of the lumbar panel may flex relative to the spinal frame. While the spinal frame can be shaped according to an individual's anatomy, it is also provided to assure additional rigidity to ensure that the wearer's back can be pulled into extension. Alternatively, the spinal frame may be formed by injection molding a plastic covering over the metal strut.

A soft plastic or other suitable material may be attached to or formed on the lower end of the spinal frame to serve as a cushion element 25 for a wearer's sacrum. A method for forming a metallic frame within an overmolded plastic or various plastic layers is described more fully in U.S. Pat. No. 7,727,174, granted on Jun. 1, 2010, and incorporated by reference. Yet another alternative is hot forming the spinal frame under known materials and principles.

Figure 10:
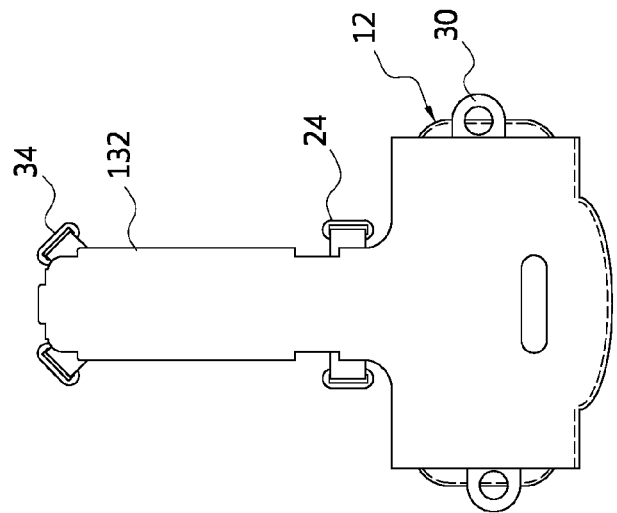
FIG. 10 is an exterior view of the posterior frame assembly and lumbar panel of FIG. 6 with the padding of FIG. 8 mounted thereon.
Figure 9:
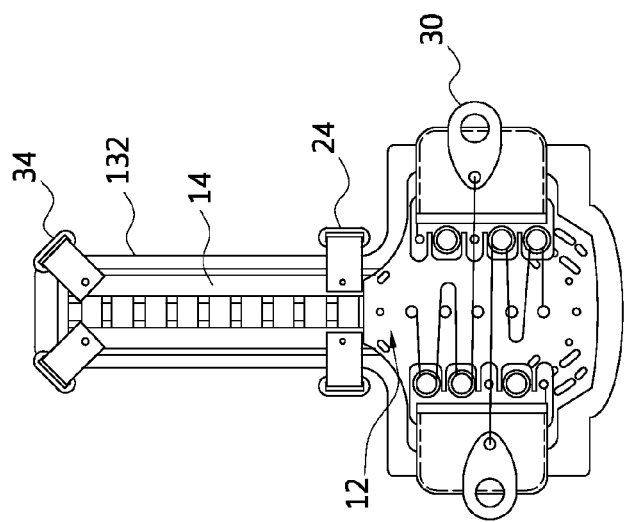
FIG. 9 is an interior view of the posterior frame assembly and lumbar panel of FIG. 6 with the padding of FIG. 8 mounted thereon.
Figure 8:
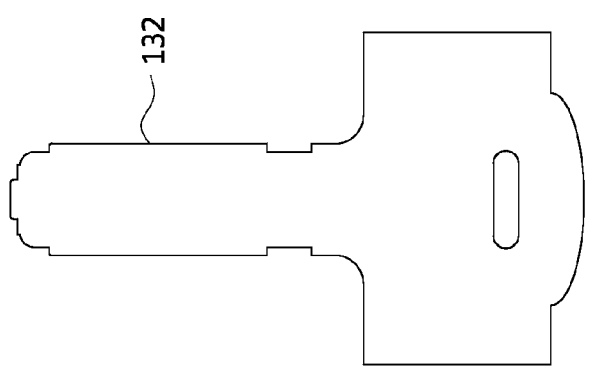
FIG. 8 is an elevational view of padding for the posterior frame assembly and lumbar panel of FIG. 6.

In observing FIGS. 8-10, the orthosis 10 may include a cover that is dimensioned and configured to extend beyond the lumbar assembly 12 and the spinal frame 14. The cover 132 is located adjacent the wearer, and generally follow the contours of the lumbar assembly 12 and spinal frame 14. The lower and upper brace assemblies 24, 34 may extend in part beyond the periphery of the cover 132, and the handles 30 of the lumbar assembly 12.

In this embodiment, the spinal frame 14 is located along the inside of the lumbar assembly 12 so the spinal frame is located between the lumbar assembly 12 and the wearer's back when the spinal orthosis is worn. The padding may comprise a strip only corresponding to the spinal frame and may not necessarily cover the entire spinal frame and the lumbar assembly. Alternatively, padding may be provided over the entire spinal frame and the lumbar assembly.

The middle bracket assembly 24 includes at least two brackets 26 extending from opposed side portions of the spinal frame 14 and pivoting about pivot points 27. The bracket assembly 24 is located particularly above the lumbar support 32, and the brackets 26 individually pivot at least above the lumbar support 32 in directions toward the upper and lower portions of the spinal frame. The upper bracket assembly 34 likewise has at least two brackets 36 that extend from opposed side portions of the spinal frame 14 at the upper portion, preferably the uppermost end of the upper portion, and similarly rotate about pivot points 37. The pivoting nature of the bracket assemblies is such that they conform to the anatomy of the wearer and can be oriented at angles that facilitate tightening of the strap assemblies.

Each of the bracket assemblies includes the brackets 26, 36 and extensions 29, 39 secured to the spinal frame and carry the brackets 26, 36. The extensions may be flexible to conform to the anatomy of the wearer or alternatively they may be rigid or semi-rigid. The brackets are preferably D-rings sized accordingly to receive the straps.

The spinal frame 14 may come in predetermined sizes, or in the alternative may be selectively reducible in size. In one variation, the spinal frame 14 may include a plurality of key hole slots along its length, and the lumbar support includes a plurality of locking tabs which permit selective placement of the length of the spinal frame 14 relative to the lumbar frame, as particularly taught in U.S. patent publication 2011/0105971, published on May 5, 2011, incorporated by reference.

Figure 11:
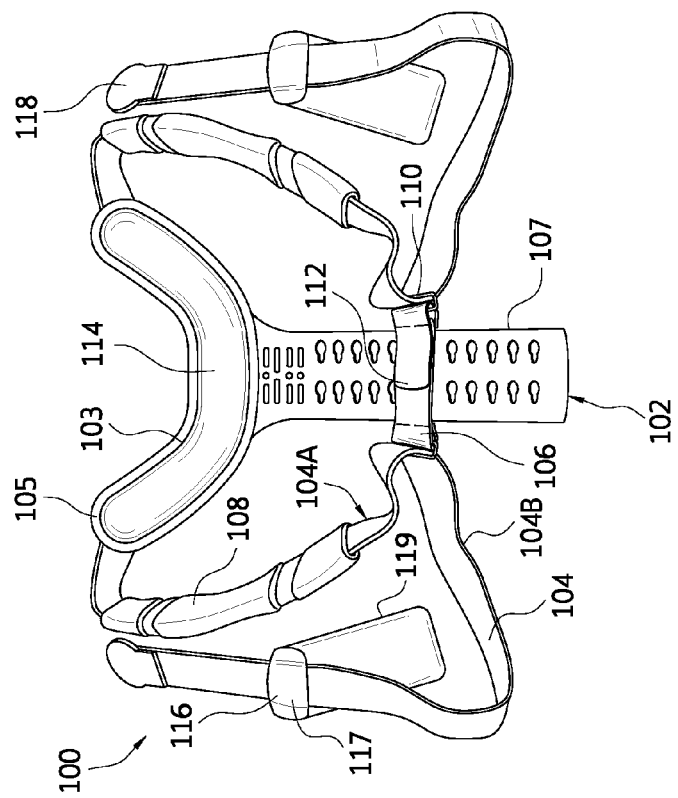
FIG. 11 is a schematic view of another embodiment of a posterior frame assembly having an adjustable strap system.

In an example shown by FIG. 11, another embodiment of the posterior frame assembly 100 includes a posterior frame 102 and a strap assembly 104 connected to the frame 102. The strap assembly 104 adjustably secures to a pair of arms 105 depending from a generally U-shaped or alternatively shaped upper portion 103 of the frame 102 with padding 114 provided along the upper portion.

Figure 12:
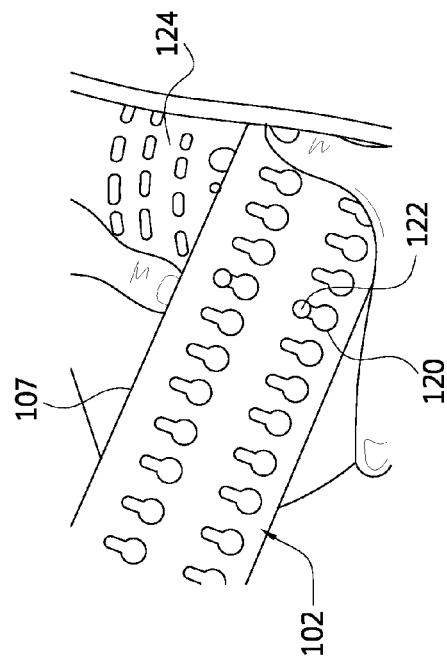
FIG. 12 is a schematic view of attaching the posterior frame assembly of FIG. 11 to a panel.
Figure 13:
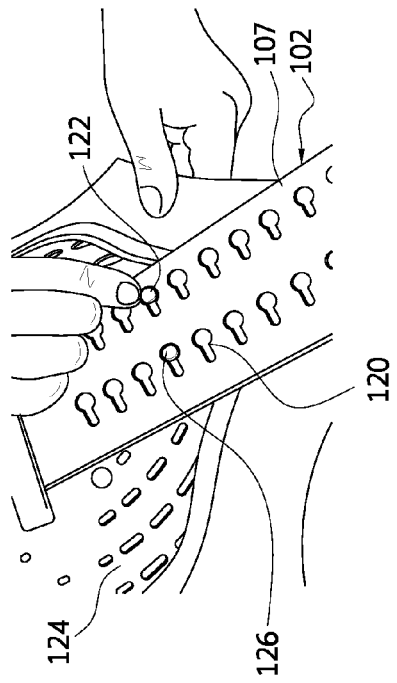
FIG. 13 is a schematic view of providing locking tabs on the posterior frame assembly and the panel of FIG. 12.

As shown in FIGS. 12 and 13, the posterior frame 102 may be removably mounted onto a panel 124, whether a rigid panel or a panel for use with the lumbar assembly described. The extension 107 of the posterior frame 102 defines a plurality of keyhole slots 120 that secure to pegs 122 extending from the panel 124. To maintain the pegs 122 within the keyhole slots 120, keyhole caps 126 may be placed within the keyhole slots 120 and wedge against the corresponding peg to prevent the extension 107 from becoming loose from the panel 124.

Referring to FIG. 11, the strap assembly 104 defines a pair of strap segments 104A extending from the arms 105 to a slidable strap mount 106 located along an elongate extension 107 that may correspond to a posterior thoracic extension. The strap mount 106 defines a pair of brackets 110 on opposed sides of the extension 107 through which the strap segments 104A extend. The strap mount 106 can adjustably slide along the extension 107 to an appropriate location to suit the needs of the wearer.

The strap mount 106 can be tensioned at strap ends 112, or opened for removal from the extension at the strap ends 112 which removably secure to one another. An elongate strap pad 108 may cover at least part of the strap segment 104A to provide additional padding to the chest and shoulder of the wearer when the strap segment 104A is tensioned. The strap assembly 104 defines a strap segment 104B which can be secured to the belt segments 38, as similarly shown in FIG. 1, by strap ends or tabs 118.

Figure 14:
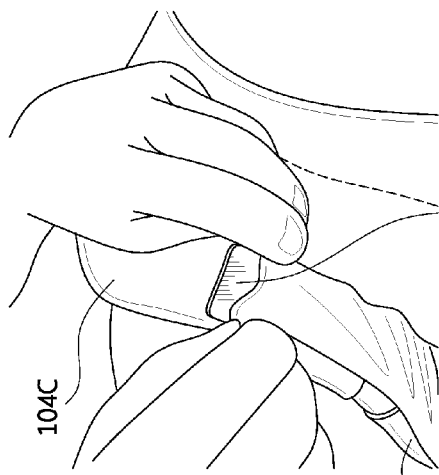
FIG. 14 is a schematic view of adjusting the strap assembly of FIG. 11.
Figure 15:
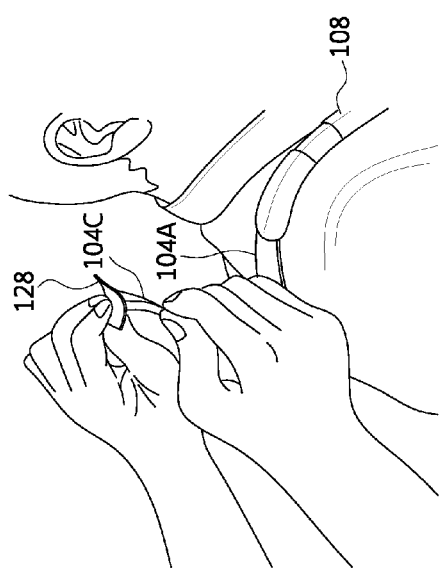
FIG. 15 is a schematic view showing a padding cover for the strap assembly of FIG. 1.

FIGS. 14 and 15 depict adjustment of the strap assembly 104 with a strap segment 104C extending from the arms 105 and securing onto the strap segment 104A to adjust the length of the strap assembly at the upper portion 103 of the frame 102. A strap tab 128, preferably having an alligator clip with opposed sides of hook material arranged for clamping and securing onto loop material of the strap segment 104C, is adjustably secured to the strap assembly 104. At an initial fitting of the orthosis, the clinician can trim the length of the strap assembly and then secure the strap tab 128 onto the trimmed strap assembly. The strap tab 128 is secured by hook fasteners onto a surface of the strap segment 104A.

A strap padding sleeve 108 slidably adjusts along the strap segment 104A, and provides additional cushioning for the wearer when the strap assembly 104 is tensioned and urged against the shoulders and chest of the wearer. The padding sleeve 108 is adjusted to slide over the strap tab 128 to conceal the strap tab 128, and minimize the strap tab 128 from catching on the clothing of the wearer.

Figure 16:
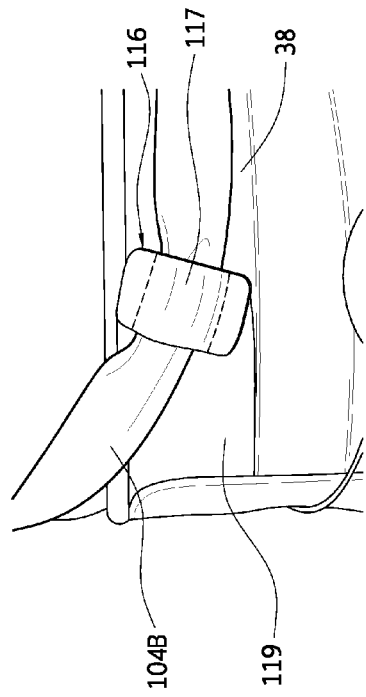
FIG. 16 is a schematic view of the strap guide of FIG. 11 on a belt segment.

FIGS. 11 and 16 depict the strap assembly 104 as including strap guides 116 having a loop 117 through which the strap segment 104B passes through, and a base portion 119 for affixation onto side portions of the belt segments 38. The strap segment 104B slides through the loop 117 and the base portion 119 allows for adjustment of the strap segment 104B according to the anatomy of the wearer and to assure proper location of securing the tabs 118 on the belt segment 38.

Figure 18:
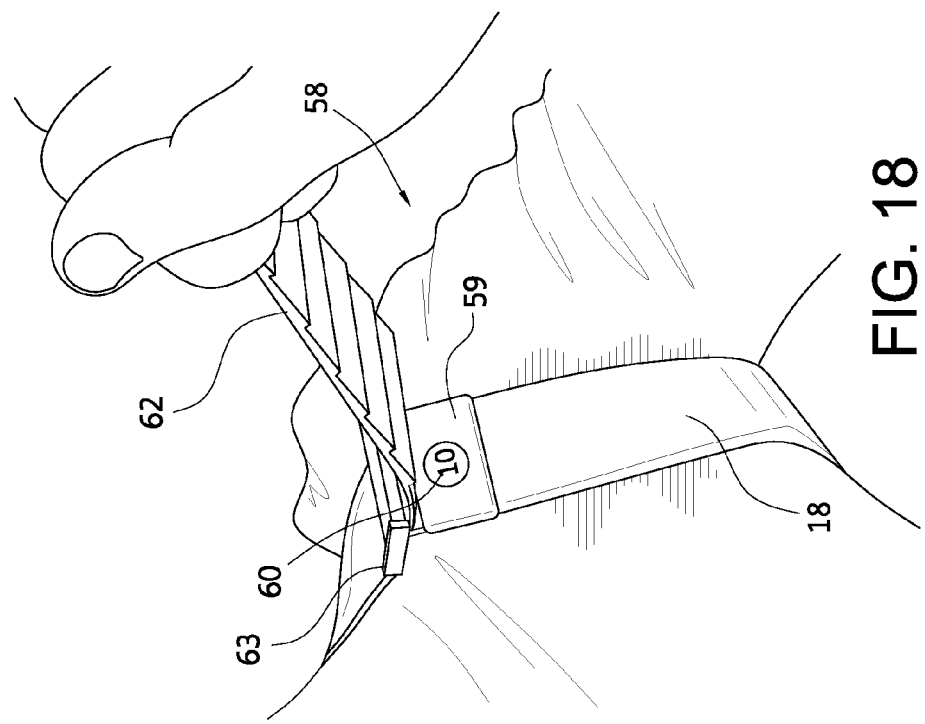
FIG. 18 is another schematic view of the strap assembly of FIG. 17.
Figure 17:
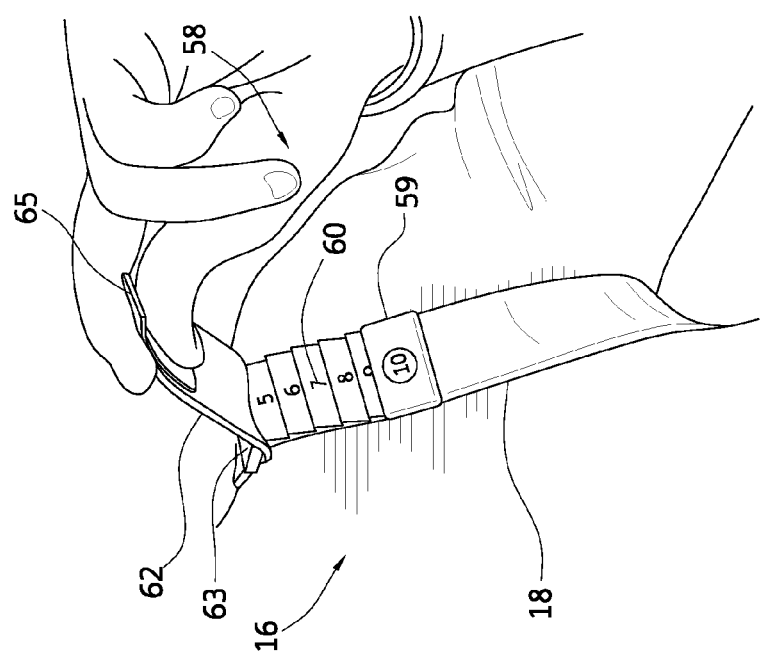
FIG. 17 is a schematic view of another embodiment of a strap assembly for the spinal orthosis of FIG. 1.

As shown in FIGS. 17 and 18, another embodiment of the strap assembly 16 may include a dosing system 58. In the example shown, the strap assembly is tightened by pulling the strap 18 from near or at the shoulder, the dosing system 58 involves pulling the strap end 62 back through a bracket assembly 63. Depending on the needed travel and the final placement of the strap end 62, a clip or handle 65 is used for grasping to pull the strap 18 downward to affix it to the strap. If the strap end 62 ends in the armpit, one can remove the clip 65 and simply let the strap hang so it is not too difficult for the wearer to attach and deattach.

A plurality of indicia 60, such as numbers, are displayed on the strap to represent relative tightening levels on the strap. A removable tab or stopper 59 with a window is then placed on the appropriate number by a clinician, where a number, such as 10 in the depicted example, indicates a dosing level, such as in maximum tension or a maximum tightening level of the strap 18.

In an example, the strap end 62 is pulled by the wearer until the tab or stopper 59 prevents the strap from going any further. That way, it is ensured that the dosing is correct without the wearer having to look at the numbers. This may be advantageous for wearers with chronic pain of the back and having sensitivity to pressure on the impaired back.

Figure 19:
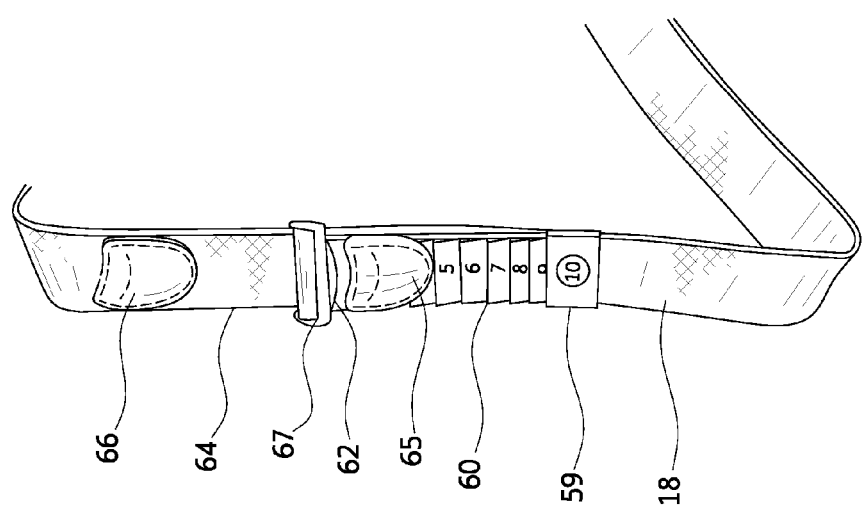
FIG. 19 is a schematic view of a variation of the strap assembly of FIG. 17.

In another strap assembly embodiment of FIG. 19, a buckle 67 is located along or adjacent the shoulder (whether on the anterior side, as shown, or on the posterior side of the shoulder) makes it easier for the wearer to adjust the strap rather than a D-ring. The buckle 67 makes it so the wearer need not hold the strap 18 while placing the strap end 62 down onto the strap. The strap end and the strap engage one another by known means, such as by hook and loop fasteners.

The strap assembly includes an intermediary strap 64 connecting to the spinal frame via one of the upper bracket assemblies discussed above. A tab 66 preferably has two flaps connected at one end, and have opposed faces with hook material so the flaps can enclose an end of the intermediary strap 64 by sandwiching a strap end of the intermediary strap 64 having hook receivable material to allow for a firm grasp of the strap. This arrangement is able to adjust the strap so the buckle 67 rests on top of the shoulders, slightly to the front, to assure the pull is easiest for the wearer since this reduces friction between the strap and buckle.

Figure 20:
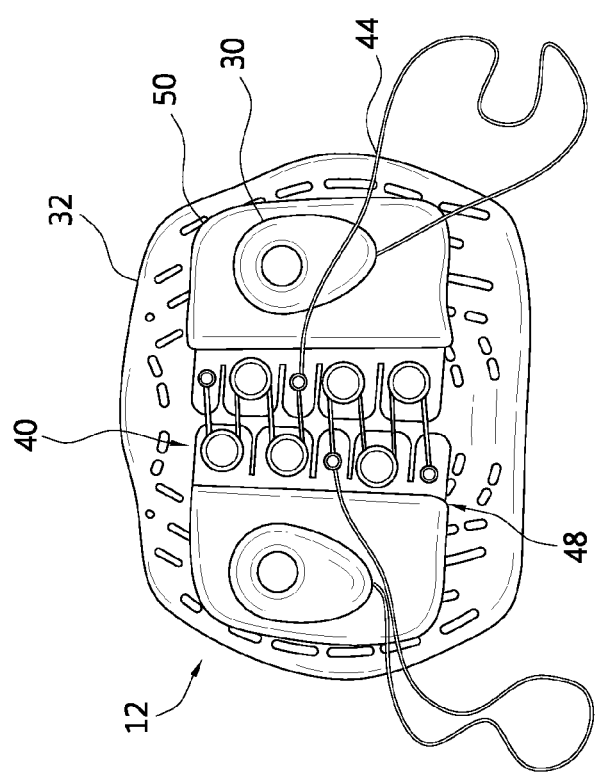
FIG. 20 is a schematic view of the compression system in the lumbar assembly for the spinal orthosis of FIG. 1.

FIG. 20 illustrates a compression system 40 belonging to the lumbar assembly and having tensioning elements 44 (similar to tensioning element 28) carrying handles 30 extending alongside each of the belt segments 38A, 38B in FIG. 1. The compression system 40 has mounts 48 that slide relative to a lumbar panel 32 and individually secure to the belt segments via attachments 50. The lumbar assembly may include anterior panels that are securable to an anterior portion of the belt segments. The lumbar assembly 12 may be a known assembly or one modified under U.S. patent application publication 2010/0217167, published on Aug. 26, 2010, and U.S. Pat. No. 8,172,779, granted on May 8, 2012, and incorporated by reference.

Figure 21:
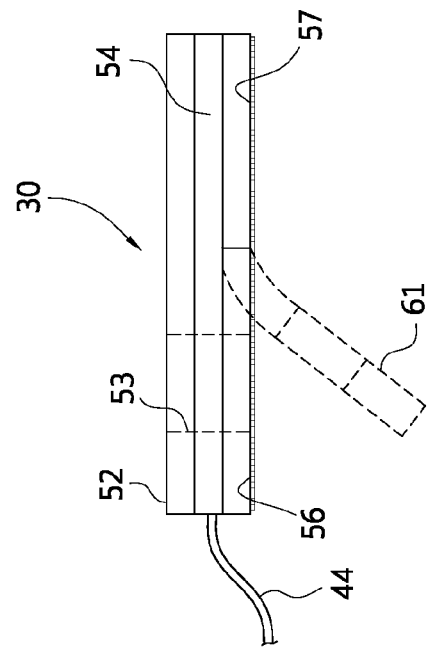
FIG. 21 is a cross-sectional schematic view of a handle for the spinal orthosis of FIG. 20.

In reference to FIG. 21, the handle 30 may comprise a soft structure constructed from at least three layers. The top layer 52 is a soft loop material so another handle can attach on top of this surface and hence the handle itself. A bottom layer 56 is constructed from a hook material having hook elements used to attach it to the belt segments. The center layer is a plastic layer 54 that attaches to the tensioning element or drawstring from the compression system.

The handle 30 defines an opening 53 through which a finger may be extended therethrough to simplify pulling of the tensioning element. The top layer 52 or other suitably soft material may extend about the periphery to provide a cushion about the opening. The strap ends of the strap assembly may likewise have a similar construction to the handle including the opening to facilitate pulling of the straps and affixation.

The bottom layer 56 may be configured so that only a portion 57 is secured against the plastic layer 54. A portion 61 of the bottom layer 56 does not secure to the plastic layer 54 and corresponds to the opening 53. When removing the handle from the belt segments, the wearer can slip a thumb through the opening 53, and have better leverage by fully extending a thumb or finger through the opening 53. The handle 30 is detached from the belt segments by peeling the hook elements of the bottom layer 56 downward and then outward for easy removal of the handle from the belt segments.

According to this embodiment, the handle is advantageous in that it is generally flexible and resilient so it can generally conform to the wearer's anatomy when secured over the belt segments but is also sufficiently durable to withstand forces exerted thereon when used to pull the tensioning elements. The handle is further advantageous in that it is sufficiently soft to enable easy use by geriatric or arthritic wearers.

Figure 22:
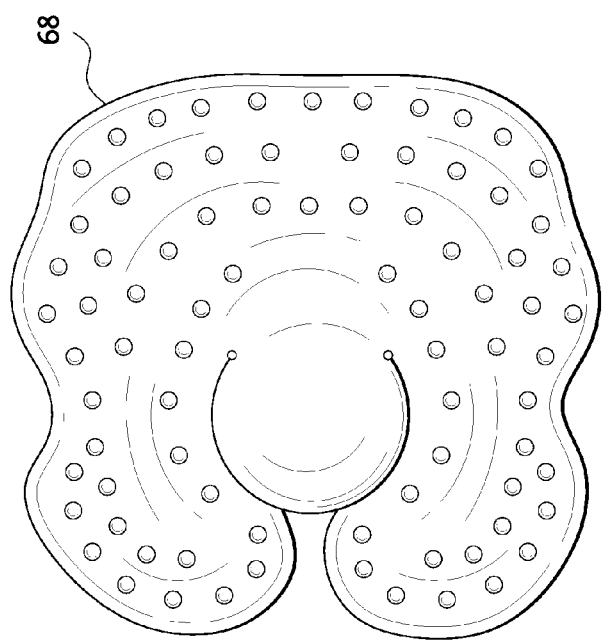
FIG. 22 is a schematic view of a bladder for the spinal orthosis of FIG. 1.

FIG. 22 depicts an air bladder pad 68 that may be inserted into the cover 46 of the lumbar support to provide a dynamic padding element on the inside of the spinal orthosis, particularly against the spinal frame. The pad may be preinflated or adjustable so the wearer can inflate the pad to a given level, or alternatively the pad may be a foam or of similar construction that the wearer can selectively place between the cover and the spinal frame when necessary.

According to FIG. 23, the spinal orthosis includes a consistent donning system that ensures that the wearer always places tension on the strap assembly in a consistent manner. The practitioner can set the strap assembly so that when placed on the wearer, it will exert the same tension. This has practical benefits in that the practitioner can regulate the tension in the strap assembly, and takes the guesswork away from the wearer to prevent over tightening of the strap assembly, and potential deleterious usage of the spinal orthosis.

Figure 24:
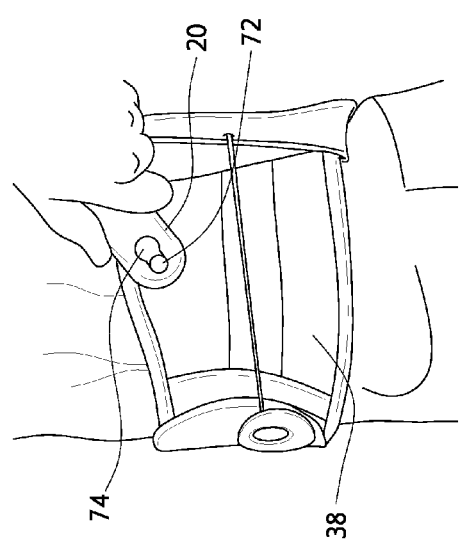
FIG. 24 is a schematic view showing an attachment point for temporary attachment on a side of the belt segment.

The embodiment of FIG. 23 employs a plurality of hooks or brackets 70, 76, 78 oriented to receive the strap ends 20. The plurality of brackets may be placed at a plurality of sequential locations according to different tightening levels. Each of the brackets has a hook or pin 72 arranged to receive an opening 74 at the strap end 20. The strap end may be arranged in a manner similar to the embodiment of FIG. 21 regarding the handle, or may define a keyhole type configuration as depicted in FIG. 24.

It follows from the consistent donning system that an attachment point is created in the front or anterior side of the belt segments so that when the straps are engaged in that location, the spinal orthosis is in tension. The additional brackets serve likewise as possible attachment points at different locations that may incur more or less tension. As shown in FIG. 24, an attachment point may be provided that is used so the strap assembly is in a substantially loose configuration so the wearer can easily remove the spinal orthosis.

In reference to the embodiment of FIGS. 25 and 26, a magnetic locking system 79 is provided in which the strap end 20 includes a locking element 84 that mechanically and magnetically locks to one of a plurality of receptacles 80, 82 on the belt segments 38. The lock receptacles have a slot 90 and mount 88 that permit a pin 86 carried by the locking element to slide into the slot 90 and rest in the mount 88. Fidlock GmbH of Hannover, Germany, provides an example of a magnetic locking system by the SNAP product.

The magnetic locking system is arranged in principle similar to the consistent donning system of FIG. 14 in that the magnetic locking system in the system allows for consistent donning of the spinal orthosis, particularly affixation of the strap assembly.

Figure 27:
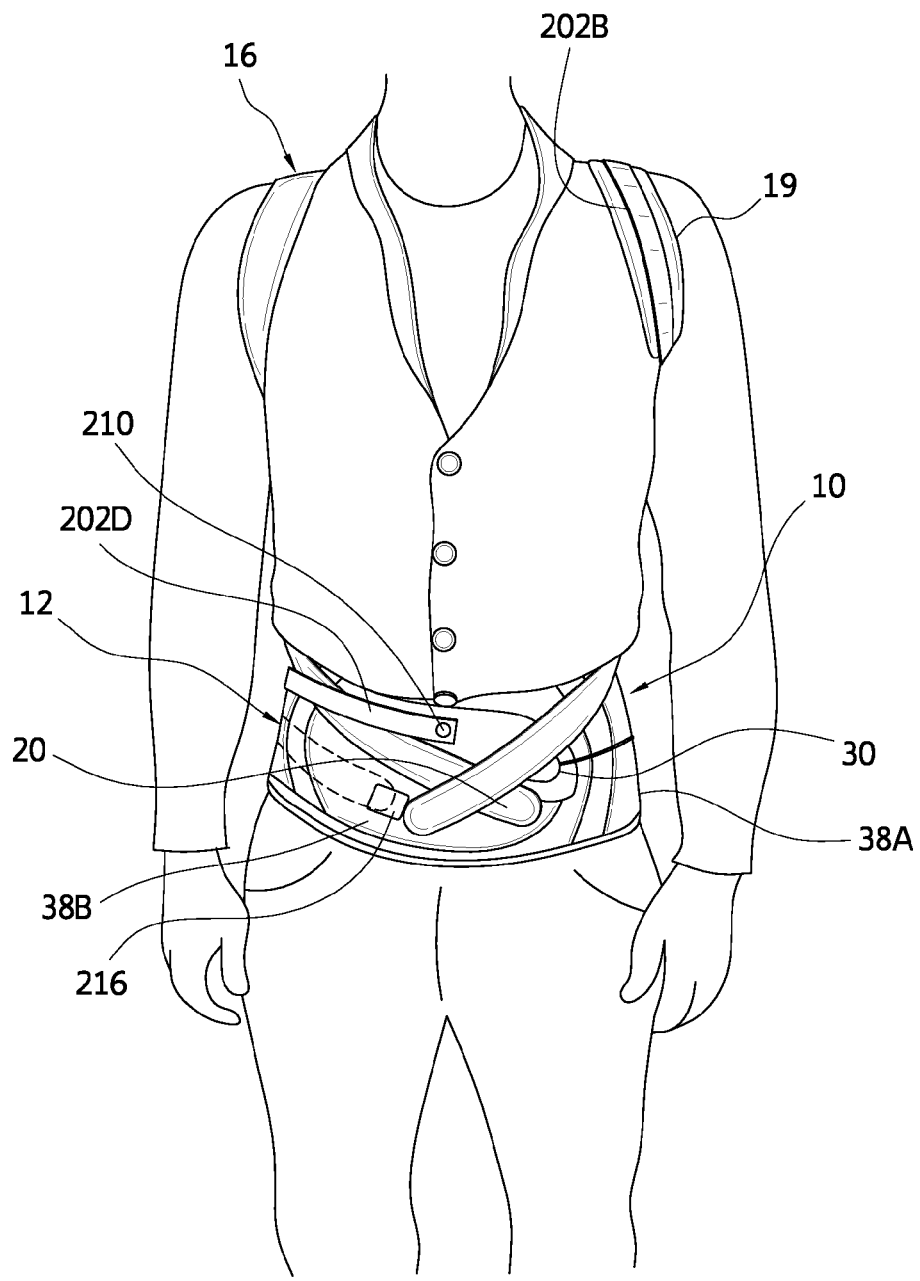
FIG. 27 is a front view of another embodiment of a spinal orthosis on a wearer including a device for treating scoliosis.
Figure 28:
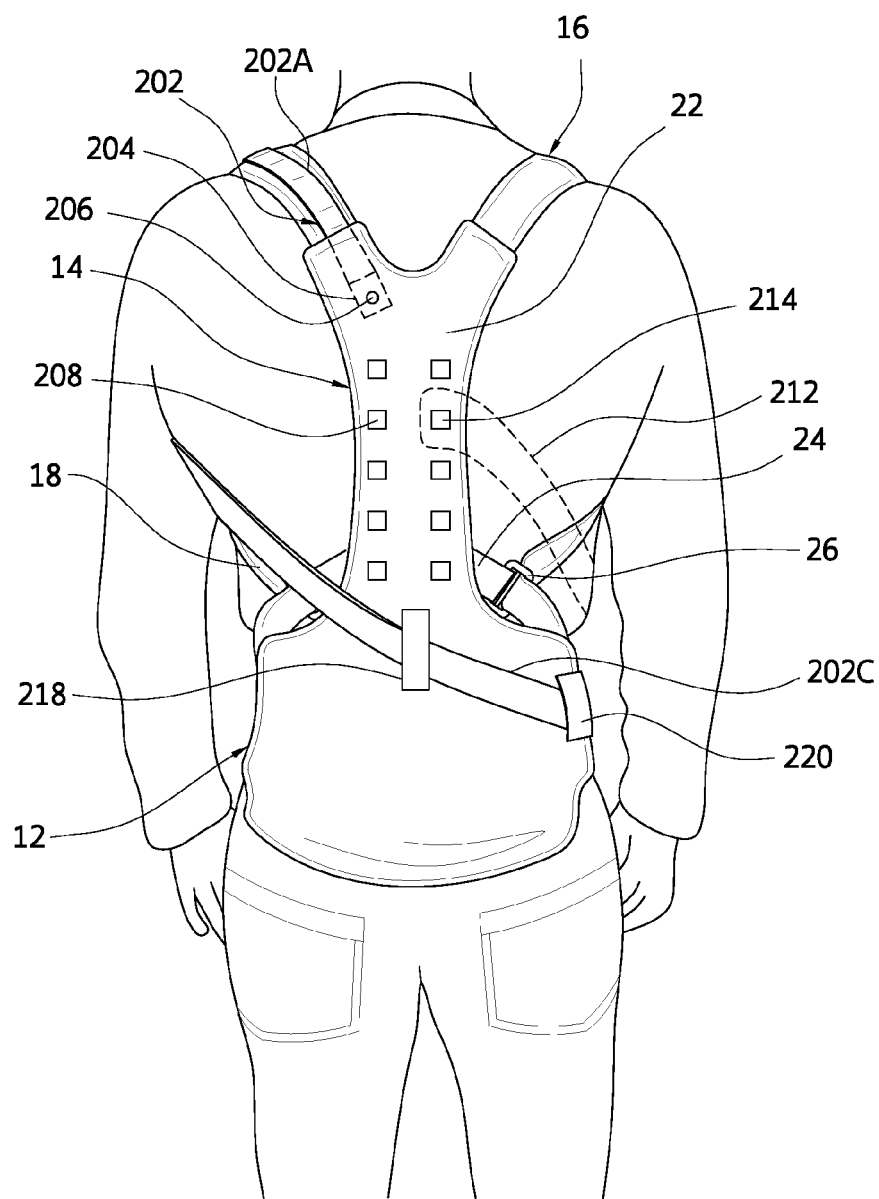
FIG. 28 is a rear view of the spinal orthosis embodiment of FIG. 27.
Figure 29:
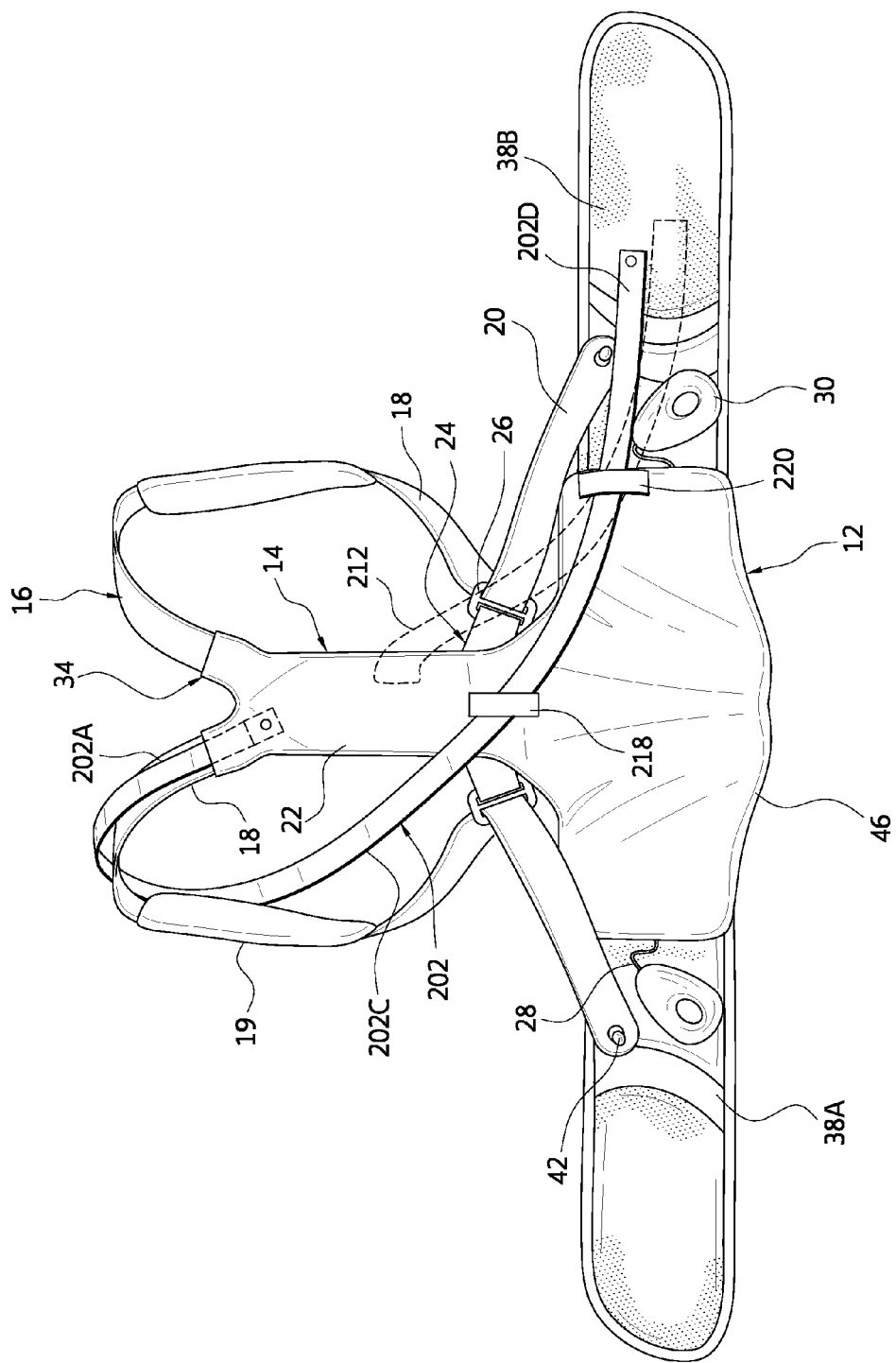
FIG. 29 is an exterior elevational view of a variation of the spinal orthosis of FIG. 27.

In the embodiment of FIGS. 27-29, the spinal orthosis of FIGS. 1-3 and the variations of FIG. 4A is arranged for treatment of scoliosis. An elastic strap 202 has a first end secured to the spinal frame 14 and a second end adjustably securing to the lumbar assembly 12.

A first variation of the elastic strap 202 has a first segment 202A secured to the upper portion of the spinal frame 14, and extends over the strap 16 so as to go over the shoulder onto the anterior side of the wearer. The strap 16 carries a pad 19 over which a second segment 202B of the elastic strap may extend, and distributes any forces exerted by the elastic strap 202. The pad 19 may include a guide 222 to orient the elastic strap 202. The elastic strap 202 has a segment 202C extending to the posterior side of the wearer and across the posterior side of the lumbar assembly 12 and/or spinal frame 14. At least one guide 218, 220 may be located along the lumbar assembly 12 and/or spinal frame 14 through which the elastic strap 202 may extend. A segment 202D extends over an anterior side of the lumbar assembly 12 and adjustably secures thereto.

It follows that while a first strap segment of the strap assembly extends from the upper portion of the spinal frame and connects to a first middle bracket assembly located at the middle portion of the spinal orthosis, the elastic strap extends along the first strap segment generally to the first middle bracket assembly and further extends past the middle bracket assembly to secure to a second belt member belonging to the lumbar assembly, whereas a second strap segment extends from the first middle bracket assembly and secures to a first belt member belonging to the lumbar assembly.

The elastic strap 202 may include a bracket or tab 204 located at a first end that secures to the spinal frame. The tab 204 may carry a fastener 206 for securely and adjustably connecting to the spinal frame 14. The spinal frame 14 may include a plurality of openings or brackets 208 arranged along its length by which the first end of the elastic strap 202 may removably secure. The openings or brackets 208 allow a clinician to selectively attach the elastic strap first end among a plurality of locations in order to adjust the strap to the specific needs of the wearer. The openings or brackets 208 may extend through or over the cover 22 of the spinal frame 14.

The various brackets 208 may be constructed in a similar manner as the attachment points 76, 78, and the second end of the elastic strap may couple to the lumbar assembly to the same attachment points as the strap assembly. Alternatively, the elastic strap may include other fastener means, such as hook and loop type fastener elements, to secure over a plurality of locations of the lumbar assembly. For example, in order to trim the elastic strap to size, a strap tab bearing hook elements may couple to the second end of the elastic strap, and similarly bear an extension carrying hook elements that are engageable with a hook surface of the lumbar assembly.

The spinal orthosis may be defined as having first and second sides generally defined as opposed sides of a longitudinal axis of the spinal frame. The first end of the elastic strap 202 anchors to the first side of the spinal frame 14, wraps around the first side of the wearer to extend across the posterior side of the wearer, and the second end of the elastic strap anchors to the anterior side of the lumbar assembly, preferably on the second side thereof. The elastic strap is oriented to encourage corrective movement of the spine and torso.

The spinal orthosis may include a plurality of elastic straps anchored at various locations along the spinal frame, and anchored to various locations along the lumbar assembly. Various elastic straps may be used having different tensions to encourage the desired resistance and corrective action, and may work together to stabilize or correct the spine. The straps of the strap assembly may be inelastic so that the elastic strap is elastically movable relative to the strap assembly.

In another embodiment of the elastic strap, FIGS. 27-29 show an elastic strap 212 securing to both the second side of the spinal frame 14 and connecting to a second side of the lumbar assembly 12. The elastic strap 212 has a first end 214 that may similarly secures to the spinal frame 14 as the elastic strap 202. In any of the embodiments, the elastic strap may be arranged on either the first or second sides of the spinal frame, at any number of heights along the spinal frame. Moreover, the elastic straps 202 and 212 may be used in combination with one another, with additional elastic straps, or in combination with inelastic straps including those in the strap assembly or in supplement to the strap assembly.

According to a method for using the spinal orthosis of FIGS. 27-29, the method employs the aforementioned spinal orthosis, and further includes the steps of securing a first end of an elastic strap to the spinal frame within the upper or middle portions and along a posterior side of a wearer, and securing a second end of the elastic strap to one of the first and second belt segments on the anterior side of the lumbar assembly. The method may include guiding the elastic strap through a strap guide connected to the spinal orthosis toward the one of the first and second belt segments.

It should be understood that not necessarily all objects or advantages may be achieved under any embodiment of the invention. For example, those skilled in the art will recognize that the invention may be embodied or carried out to achieve or optimizes one advantage or group of advantages as taught without achieving other objects or advantages as taught or suggested.

Those skilled in the art will recognize the interchangeability of various disclosed features. Besides the variations described, other known equivalents for each feature can be mixed and matched by one of ordinary skill in this art to construct spinal orthosis under principles of the present invention.

Although this invention has been disclosed in certain exemplary embodiments and variations, it therefore will be understood by those skilled in the art that the present invention extends beyond the disclosed embodiments to other alternative embodiments and/or uses of the invention and obvious modifications and equivalents. It is intended that the scope of the present invention disclosed should not be limited by the disclosed embodiments described above.

The invention claimed is:

1. A spinal orthosis having anterior and posterior sides divided by an anterior-posterior plane, the orthosis comprising:
    an elongate and substantially rigid spinal frame having upper, middle and lower portions, and having first and second lateral sides, the spinal frame located on the posterior side;
    a lumbar assembly connected to the lower portion of the spinal frame and extending across the posterior and anterior sides;
    a strap assembly having a first end secured to the upper portion of the spinal frame and a second end adjustably securing to the lumbar assembly; and
    an elastic strap having a first end secured to the spinal frame and a second end adjustably securing to the lumbar assembly;

at least one strap guide connected to the spinal frame or lumbar support on the posterior side, the elastic strap slidably extending through the strap guide and being directed toward the anterior side of the lumbar assembly.

2. The spinal orthosis of claim 1, wherein the strap assembly includes a first strap segment extending from the upper portion of the spinal frame to a first middle bracket assembly located at the middle portion of the spinal orthosis, and a second strap segment directed from the first middle bracket assembly and securing to the lumbar assembly.

3. The spinal orthosis of claim 2, wherein the lumbar assembly has first and second belt members extending from the first and second lateral sides of the spinal frame, respectively, the first strap segment extends from the upper portion of the spinal frame at the first side and the second strap segment secures to the first belt member.

4. The spinal orthosis of claim 3, wherein the elastic strap extends from the upper portion of the spinal frame and secures to the second belt member.

5. The spinal orthosis of claim 1, further comprising a pad located on the strap assembly, the elastic strap extending over the pad and the strap assembly.

6. The spinal orthosis of claim 5, wherein the pad defines a guide through which the elastic strap extends, the elastic strap adjustably stretching relative to the guide and the strap assembly.

7. The spinal orthosis of claim 1, further comprising at least one attachment point mounted to and extending from an end portion of the lumbar assembly, the strap assembly engaging the at least one attachment point.

8. The spinal orthosis of claim 7, wherein the second end of the strap assembly engages the at least one attachment point.

9. The spinal orthosis of claim 1, wherein the first end of the elastic strap is secured to a first lateral side of the spinal frame, and the second of the elastic strap secures to a first belt member of the lumbar assembly extending from a second lateral side of the spinal frame opposite the first lateral side.

10. The spinal orthosis of claim 9, wherein the elastic strap is adjustably securable along a height of the spinal frame within the upper and middle portions of the spinal frame.

11. The spinal orthosis of claim 1, wherein a first strap segment of the strap assembly is inelastic, and the elastic strap is elastically movable relative to the first strap segment.

12. The spinal orthosis of claim 1, wherein the strap assembly includes a first strap segment extending from the upper portion of the spinal frame and connects to a first middle bracket assembly located at the middle portion of the spinal orthosis and a second strap segment extending from the middle bracket assembly to a first belt member belonging to the lumbar assembly, the elastic strap extending along the first strap segment generally to the first middle bracket assembly and further extending past the middle bracket assembly to secure to a second belt member belonging to the lumbar assembly.

13. The spinal orthosis of claim 1, wherein the elastic strap is arranged to secure at a plurality of locations along a height of the spinal frame defined at least in part between the upper and middle portions.

14. A method for securing a spinal orthosis to a wearer, the spinal orthosis having anterior and posterior sides divided by an anterior-posterior plane, and comprising a rigid spinal frame arranged along the posterior side and defining upper, middle and lower portions, and a lumbar assembly connected to the lower portion of the spinal frame along a posterior side of the lumbar assembly, the lumbar assembly having first and second belt segments extending from the posterior side to the anterior side of the spinal orthosis, the method comprising the steps of:
securing a first end of an elastic strap to the spinal frame within the upper or middle portions;
extending the second end of the elastic strap to the anterior side and then guiding the elastic strap through a strap guide connected to the spinal orthosis or lumbar assembly on the posterior side and toward one of the first and second belt segments such that the elastic strap slidably extends through the strap guide;
extending the second end of the elastic strap from the strap guide toward the anterior side;
securing a second end of the elastic strap to one of the first and second belt segments on the lumbar assembly.

15. The method of claim 14, further comprising the steps of:
pulling a first inelastic strap segment downwardly from an upper portion of a spinal frame, the first inelastic strap segment having a first end secured to the upper portion of the spinal frame;
routing the first inelastic strap segment through a bracket assembly pivotally secured along a middle portion of the spinal frame;
directing a second inelastic strap segment from the bracket assembly and attaching an end of the second inelastic strap segment to the lumbar assembly.

16. The method of claim 15, wherein the elastic strap has a first segment extending along the first inelastic strap segment from the upper portion of the spinal frame to the bracket assembly, the elastic strap having a second segment extending past the bracket assembly over a surface of the spinal frame, the elastic strap having a third segment extending along a portion of one of the first and second belt members.

17. The method of claim 14, further comprising the step of:
wherein the first end of the elastic strap is secured to a first lateral side of the spinal frame, and the second end of the elastic strap secures to the second belt member of the lumbar assembly extending from a second lateral side of the spinal frame opposite the first lateral side.

18. A spinal orthosis comprising:
an elongate and substantially rigid spinal frame having upper, middle and lower portions;
a lumbar assembly connected to the lower portion of the spinal frame;
a strap assembly secured to the upper portion of the spinal frame and adjustably secured to the lumbar assembly; and
an elastic strap having a first end secured along either of the upper or middle portions of the spinal frame and extending obliquely toward the lumbar assembly, and a second end of the elastic strap adjustably securing to the lumbar assembly, the elastic strap slidably extending over at least part of the strap assembly;
wherein the first end of the elastic strap is secured to a first lateral side of the spinal frame, and the second end secures to a first belt member of the lumbar assembly extending from a second lateral side of the spinal frame opposite the first lateral side.

19. The spinal orthosis of claim 18, wherein the strap assembly includes at least one inelastic strap, the elastic strap elastically moveable relative to the inelastic strap.

* * * * *